United States Patent
Ottoboni et al.

(10) Patent No.: US 11,844,837 B2
(45) Date of Patent: Dec. 19, 2023

(54) COMPOSITIONS OF A POLYORTHOESTER AND AN ORGANIC ACID EXCIPIENT

(71) Applicant: Heron Therapeutics, Inc., San Diego, CA (US)

(72) Inventors: Thomas B. Ottoboni, Belmont, CA (US); Lee Ann Lynn Girotti, San Bruno, CA (US)

(73) Assignee: Heron Therapeutics, Inc., San Diego, CA (US)

( * ) Notice: Subject to any disclaimer, the term of this patent is extended or adjusted under 35 U.S.C. 154(b) by 367 days.

(21) Appl. No.: 17/209,078

(22) Filed: Mar. 22, 2021

(65) Prior Publication Data

US 2021/0205458 A1    Jul. 8, 2021

Related U.S. Application Data

(63) Continuation of application No. 14/691,491, filed on Apr. 20, 2015, now Pat. No. 10,980,886.

(60) Provisional application No. 61/982,300, filed on Apr. 21, 2014.

(51) Int. Cl.
| | | |
|---|---|---|
| A61K 47/34 | (2017.01) | |
| A61K 31/445 | (2006.01) | |
| A61K 47/12 | (2006.01) | |
| A61K 9/00 | (2006.01) | |
| A61K 31/245 | (2006.01) | |
| A61K 31/47 | (2006.01) | |
| A61K 31/167 | (2006.01) | |
| A61K 31/00 | (2006.01) | |

(52) U.S. Cl.
CPC ............ *A61K 47/34* (2013.01); *A61K 9/0019* (2013.01); *A61K 9/0024* (2013.01); *A61K 31/00* (2013.01); *A61K 31/167* (2013.01); *A61K 31/245* (2013.01); *A61K 31/445* (2013.01); *A61K 31/47* (2013.01); *A61K 47/12* (2013.01)

(58) Field of Classification Search
CPC .... A61K 47/34; A61K 9/0019; A61K 9/0024; A61K 31/00; A61K 31/167; A61K 31/245; A61K 31/445; A61K 31/47; A61K 47/12
See application file for complete search history.

(56) References Cited

U.S. PATENT DOCUMENTS

| | | |
|---|---|---|
| 4,079,038 A | 3/1978 | Choi et al. |
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,304,767 A | 12/1981 | Heller et al. |
| 4,549,010 A | 10/1985 | Sparer et al. |
| 4,780,319 A | 10/1988 | Zentner et al. |
| 4,946,931 A | 8/1990 | Heller et al. |
| 4,957,998 A | 9/1990 | Heller et al. |
| 5,968,543 A | 10/1999 | Heller et al. |
| 6,132,766 A | 10/2000 | Sankaram et al. |
| 6,613,335 B1 | 9/2003 | Ruelle |
| 7,666,914 B2 | 2/2010 | Richlin et al. |
| 8,182,835 B2 | 5/2012 | Kim et al. |
| 8,252,304 B2 | 8/2012 | Ng et al. |
| 8,367,733 B2 | 2/2013 | Burch et al. |
| 8,834,921 B2 | 9/2014 | Kim et al. |
| 8,920,820 B2 | 12/2014 | Folger et al. |
| 9,694,079 B2 | 7/2017 | Ottoboni et al. |
| 9,801,945 B2 | 10/2017 | Ottoboni et al. |
| 10,098,957 B2 | 10/2018 | Ottoboni et al. |
| 10,213,510 B2 | 2/2019 | Ottoboni et al. |
| 10,632,199 B2 | 4/2020 | Ottoboni et al. |
| 10,898,575 B2 | 1/2021 | Ottoboni et al. |
| 10,980,886 B2 | 4/2021 | Ottoboni et al. |
| 11,083,730 B2 | 8/2021 | Ottoboni et al. |
| 11,083,797 B2 | 8/2021 | Ottoboni et al. |
| 11,413,350 B2 | 8/2022 | Ottoboni et al. |
| 2002/0037300 A1 | 3/2002 | Ng et al. |
| 2002/0168336 A1 | 11/2002 | Ng et al. |
| 2005/0079202 A1 | 4/2005 | Chen et al. |
| 2006/0100160 A1 | 5/2006 | Xu et al. |
| 2007/0264338 A1* | 11/2007 | Shah .................... A61K 9/0014 514/169 |
| 2007/0264339 A1 | 11/2007 | Shah et al. |
| 2007/0265329 A1 | 11/2007 | Devang et al. |
| 2008/0145427 A1 | 6/2008 | Berchielli et al. |
| 2008/0293703 A1 | 11/2008 | Richlin et al. |
| 2008/0299168 A1 | 12/2008 | Dadey et al. |
| 2009/0124952 A1 | 5/2009 | Berman |
| 2010/0015049 A1 | 1/2010 | Wohabrebbi |

(Continued)

FOREIGN PATENT DOCUMENTS

| | | | |
|---|---|---|---|
| EP | 0795329 A1 | 9/1997 | |
| GB | 2481018 A * | 12/2011 | ............ A61K 31/00 |

(Continued)

OTHER PUBLICATIONS

Einmahl et al., "A new poly(ortho ester)-based drug delivery system as an adjunct treatment in filtering surgery", Inv. Ophthalmol. Vis. Sci., vol. 42, No. 3, pp. 695-700 (2013).

Elhakim et al., "Effects of intraperitoneal lidocaine combined with intravenous or intraperitoneal tenoxicam on pain relief and bowel recovery after laparoscopic cholecystectomy", Acta Anaesthesiol. Scand., vol. 44, No. 8, pp. 929-933 (2000).

Heller et al., "Preparation of polyacetals by the reaction of divinyl ethers and polyols", J. Polymer Sci.: Polymer Letters Ed., vol. 18, No. 4, pp. 293-297 (1980).

(Continued)

*Primary Examiner* — Jeffrey S Lundgren
*Assistant Examiner* — Ibrahim D Bori
(74) *Attorney, Agent, or Firm* — McDermott Will & Emery LLP; Judy M. Mohr; Peter Brunovskis

(57) ABSTRACT

Delivery systems and compositions comprised of a biodegradable polyorthoester polymer, an organic acid excipient, and a basic drug are described, along with related methods.

9 Claims, 2 Drawing Sheets

(56) References Cited

U.S. PATENT DOCUMENTS

| | | |
|---|---|---|
| 2010/0041765 A1 | 2/2010 | Campbell et al. |
| 2010/0305160 A1 | 12/2010 | Brummett |
| 2010/0305500 A1 | 12/2010 | Lambert et al. |
| 2012/0149864 A1 | 6/2012 | Alkatout et al. |
| 2012/0283253 A1 | 11/2012 | Ng et al. |
| 2013/0165429 A1 | 6/2013 | Ray, II et al. |
| 2014/0275046 A1 | 9/2014 | Ottoboni et al. |
| 2014/0275145 A1 | 9/2014 | Ottoboni et al. |
| 2014/0296282 A1 | 10/2014 | Ottoboni et al. |
| 2015/0297729 A1 | 10/2015 | Ottoboni et al. |
| 2015/0297730 A1 | 10/2015 | Ottoboni et al. |
| 2016/0375140 A1 | 12/2016 | Ottoboni et al. |
| 2017/0035777 A1 | 2/2017 | Ottoboni et al. |
| 2017/0035888 A1 | 2/2017 | Ottoboni et al. |
| 2017/0281778 A1 | 10/2017 | Ottoboni et al. |
| 2017/0304455 A1 | 10/2017 | Ottoboni et al. |
| 2018/0000947 A1 | 1/2018 | Ottoboni et al. |
| 2018/0353608 A1 | 12/2018 | Ottoboni et al. |
| 2021/0220474 A1 | 7/2021 | Ottoboni et al. |
| 2021/0330796 A1 | 10/2021 | Ottoboni et al. |

FOREIGN PATENT DOCUMENTS

| | | |
|---|---|---|
| GB | 2481018 A | 12/2011 |
| JP | 2006-213713 A | 8/2006 |
| JP | 2010-280668 A | 12/2010 |
| WO | WO 2003/059320 A1 | 7/2003 |
| WO | WO 2006/037116 A2 | 4/2006 |
| WO | WO 2010/093374 A1 | 8/2010 |
| WO | WO 2011/017195 A2 | 2/2011 |
| WO | WO 2013/101949 A2 | 7/2013 |
| WO | WO 2014/143635 A1 | 9/2014 |
| WO | WO 2015/164272 A2 | 10/2015 |

OTHER PUBLICATIONS

International Search Report from International Patent Application no. PCT/US2015/026695 dated Oct. 7, 2015, Application now published as International Publication No. WO2015/164272 dated Oct. 29, 2015.

International Search Report from International Patent Application No. PCT/US2015/026720 dated Jun. 25, 2015.

International Search Report from International Patent Application No. PCT/US2016/058312 dated May 11, 2017, 5 pages.

Kluivers-Poodt et al., "Pain behaviour after castration of piglets; effect of pain relief with lidocaine and/or meloxicam", Animal, vol. 7, No. 7, pp. 1158-1162 (2013).

Merkli et al., "The use of acidic and basic excipients in the release of 5-fluorouracil and mitomycin C from a semi-solid bioerodible poly(ortho ester)", J. Contr. Rel., vol. 33, No. 3, pp. 415-421 (1995).

Nguyen et al., "Hydrolysis of Some Poly(ortho-Ester)s in Homogenous Solutions", J. Pharm. Sci., vol. 73, No. 11, pp. 1563-1568 (1984).

Shin et al., "Drug delivery from catalyzed erodible polymeric matrices of poly(ortho ester)s", Biomaterials, vol. 5, No. 4, pp. 237-240 (1984).

Sparer et al., "Controlled Release From Erodible Poly(Ortho Ester) Drug Delivery Systems", J. Contr. Rel., vol. 1, pp. 23-32 (1984).

Tsai et al., "Comparison of postoperative effects between lidocaine infusion, meloxicam, and their combination in dogs undergoing ovariohysterectomy", Veterinary Anaesthesia and Analgesia, vol. 40, No. 6, pp. 615-622 (2013).

Nakahara et al., "Effectiveness of wound instillation for postoperative analgesia following pediatric inguinal herniorrhaphy", vol. 40, No. 5, pp. 650-653 (2004) *English Abstract*.

Seeking Alpha, "Heron Therapeutics and HTX-011 are Both Severely Undervalued", Seeking Alpha, Heron Therapeutics, Inc. (HRTX), 15 pages (2016), online article accessed from: https://seekingalpha.com/article1/3997210-heron-therapeutics-and-htxminus-011-are-severely-undervalued.

Winkle et al., "Local Administration of HTX-011, a Long-Acting Biochronomer-Based Bupivacaine/Meloxicam Combination, in Hernia Repair Provides Similar Initial Results Whether Injected, Instilled, or Both", Postgraduate Medicine, Conference Paper, Abstract 90, p. 63 (2016) *Abstract Only*.

\* cited by examiner

COMPOSITIONS OF A POLYORTHOESTER AND AN ORGANIC ACID EXCIPIENT

CROSS-REFERENCE TO RELATED APPLICATIONS

This application is a continuation of U.S. Non-Provisional patent application Ser. No. 14/691,491, filed Apr. 20, 2015, now allowed, which claims the benefit of priority to U.S. Provisional Patent Application No. 61/982,300, filed Apr. 21, 2014, each of which is herein incorporated by reference in its entirety.

TECHNICAL FIELD

The present disclosure is directed to compositions comprising a biodegradable polyorthoester, an organic acid, and a bioactive agent, as well as related systems and methods, among other things.

BACKGROUND

Polymer-based depot systems for administering an active agent are well known. These systems incorporate the active agent into a carrier composition, such as a polymeric matrix, from which the active agent is delivered upon administration of the composition to a patient.

Many factors influence the design and performance of such systems, such as the physical/chemical properties of the drug, the physical/chemical characteristics of the system's components and the performance/behavior relative to other system components once combined, and external/environmental conditions at the site of application. In designing polymer based systems for delivery of a drug, the desired rate of drug delivery and onset, the drug delivery profile, and the intended duration of delivery all must be considered.

Such considerations are particularly important when administering a drug for relief of pain, such as post-operative pain. Indeed, pain relief is of primary importance to most every patient undergoing surgery or to medical personnel treating or caring for a patient undergoing or recovering from a surgical procedure. Effective analgesia is vital for ensuring patient comfort, encouraging early mobilization, promoting earlier patient discharge from the medical setting (e.g., hospital, outpatient facility or the like), and for providing enhanced recovery times. Effective treatment of post-operative pain may also reduce the onset/occurrence of chronic pain syndromes such as fibromyalgia. One approach for providing localized, effective, long-acting relief of pain such as post-surgical pain is the utilization of a polymer-based system. However, as noted above, numerous factors can impact the design of an effective drug delivery system, such as one for treating post-operative pain. There remains a need for polymer-based compositions that can (i) overcome the drawbacks and challenges associated with the delivery of certain chemical classes of drug, and/or (ii) offer the flexibility to modulate or tailor the rate of drug release to provide a desired drug release profile. The present compositions and methods satisfy these and other needs.

BRIEF SUMMARY

In one aspect, provided herein is a composition comprising a polyorthoester, an organic acid, and a therapeutically active agent, e.g., one containing one or more amino groups, dispersed or solubilized in the composition.

In some embodiments, the active agent is an anesthetic. In some further embodiments, the anesthetic is a local anesthetic. In some embodiments, the anesthetic is an amino-amide type local anesthetic.

In yet some further embodiments, the amino-amide type local anesthetic is selected from the group consisting of bupivacaine, ropivacaine, levobupivacaine, dibucaine, mepivacaine, procaine, lidocaine, and tetracaine.

In yet some further embodiments, the therapeutically active agent is an amino-containing drug. In some related embodiments, the amino-containing drug is an amino-containing small molecule drug.

In one or more embodiments related to the foregoing, the basic active agent, i.e., the therapeutically active agent containing one or more amino groups, is added to the composition in its free base form (i.e., is not in the form of an ammonium salt).

In yet some additional embodiments, the organic acid is a C2-C12 carboxylic acid. In some other embodiments, the organic acid is a C2-C12 dicarboxylic acid. In some other embodiments, the organic acid is a C2-C8 carboxylic acid. In some other embodiments, the organic acid is a C2-C8 dicarboxylic acid.

In yet some further embodiments, the organic acid is selected from the group consisting of oxalic acid, malonic acid, succinic acid, glutaric acid, adipic acid, pimelic acid, fumaric acid, maleic acid, citric acid, acetylsalicylic acid and salicylic acid.

In one or more embodiments, the organic acid is comprised within the formulation in an amount less than an equimolar amount relative to the therapeutically active agent. In some particular embodiments, the composition comprises from about 1-95 mole percent of the organic acid relative to the therapeutically active agent.

In certain particular embodiments, the organic acid is a mono-carboxylic acid.

In one or more related embodiments, the composition comprises from about 10-80 mole percent of a mono-carboxylic acid relative to the therapeutically active agent.

In one or more additional embodiments, the organic acid is a mono-carboxylic acid or a di-carboxylic acid.

In one or more additional embodiments, the organic acid is a di-carboxylic acid or a tri-carboxylic acid.

In some additional embodiments, the composition comprises from about 10-40 mole percent of a di-carboxylic acid relative to the therapeutically active agent.

In some embodiments, the organic acid is a C2-C8, aliphatic, unsubstituted or substituted, saturated straight-chain di-carboxylic acid. In certain related embodiments, the di-carboxylic acid is selected from the group consisting of oxalic acid, malonic acid, succinic acid, glutaric acid, adipic acid, and pimelic acid.

In yet some further embodiments, the organic acid is a C2-C8 aliphatic, unsubstituted or substituted, di-carboxylic acid containing one or more elements of unsaturation (e.g., one or more double or triple bonds). In one or more particular embodiments, the organic acid is either fumaric acid or maleic acid.

In yet one or more further embodiments, the organic acid is a C2-C8 tricarboxylic acid such as the hydroxy-substituted tricarboxylic acid, citric acid.

In yet a further embodiment, the organic acid is an aromatic carboxylic acid. In a particular embodiment, the organic acid is benzoic acid or a substituted benzoic acid having, e.g., from 7 to 14 carbon atoms. Examples include acetylsalicylic acid and salicylic acid.

In yet another one or more embodiments, the organic acid is maleic acid.

In some embodiments, the composition is a semi-solid.

In some particular embodiments, the polyorthoester is selected from the polyorthoesters represented by Formulas I, II, III and IV as set forth herein below.

In yet a particular embodiment related to the foregoing, the polyorthoester is represented by Formula III as set forth herein.

In some embodiments, the polyorthoester is represented by the structure shown as Formula III,

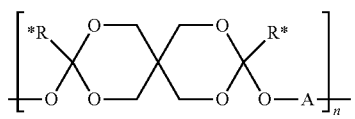

where: R* is a methyl, ethyl, propyl or butyl, n is the number of repeating units and is an integer ranging from 5 to 400, and A in each subunit is $R^1$ or $R^3$.

In some embodiments directed to Formula III, R* is ethyl.

In yet some additional embodiments directed to Formula III, A corresponds to $R^1$, where $R^1$ is

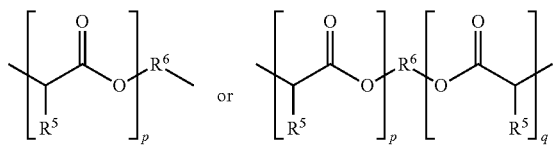

where p and q are each independently integers ranging from about 1 to 20, each $R^5$ is independently hydrogen or $C_{1-4}$ alkyl; and $R^6$ is:

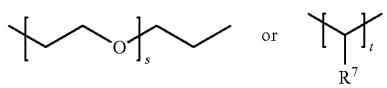

where s is an integer from 0 to 10; t is an integer from 2 to 30; and $R^7$ is hydrogen or $C_{1-4}$ alkyl.

In some other embodiments related to Formula III, R7 is C1, C2, C3, or C4 alkyl. In some particular embodiments, $R^7$ is H.

In yet still other embodiments, the $R^1$ subunits are α-hydroxy acid-containing subunits.

In yet other embodiments, p and q are each independently selected from 1, 2, 3, 4, 5, 6, 7, 8, 9, 10, 11, 12, 13, 14, 15, 16, 17, 18, 19, and 20.

In yet another embodiment, R5 is independently hydrogen, or C1, C2, C3, or C4 alkyl.

In some embodiments, A corresponds to $R^3$, where $R^3$ is:

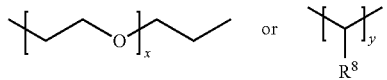

and x is an integer ranging from 1 to 100. In another embodiment, x is selected from 0, 1, 2, 3, 4, and 5; y is an integer in a range from 2 to 30; and $R^8$ is hydrogen or $C_{1-4}$ alkyl. In still another embodiment, $R^8$ is a C1, C2, C3 or C4 alkyl. In another embodiment, $R^8$ is H.

In some embodiments, the polyorthoester is one of Formula I, II, III or IV, and in particular of Formula III, in which A is $R^1$ or $R^3$, where $R^1$ is

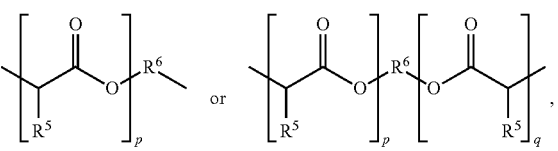

where p and q are each independently selected from 1, 2, 3, 4, 5, 6, 7, 8, 9, 10, 11, 12, 13, 14, 15, 16, 17, 18, 19, and 20 in any repeating unit, where the average number of p or the average number of the sum of p and q (p+q) is between about 1 and 7; x and s are each independently an integer ranging from 0 to 10; and t and y are each independently an integer ranging from 2 to 30. In yet additional embodiments, the sum of p and q is 1, 2, 3, 4, 5, 6 or 7 in any repeating unit of $R^1$. In yet some further embodiments, $R^5$ is H.

In yet further embodiments, A is $R^1$ or $R^3$, where $R^1$ is

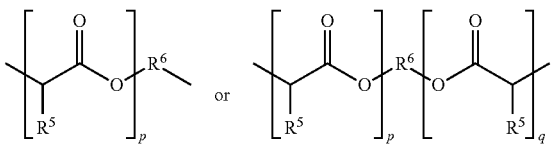

and p and q are each independently integers ranging from about 1 and 20, about 1 and 15, or about 1 and 10 in any repeating unit of $R^1$, where the average number of p or the average number of the sum of p and q (i.e., p+q) is between about 1 and 7. In another one or more embodiments, x and s each independently range from 0 to about 7 or from 1 to about 5. In still another embodiment, t and y each independently range from 2 to 10.

In one embodiment, $R^5$ is hydrogen or methyl.

In one embodiment, s and x are each independently selected from 1, 2, 3, 4, 5, 6, 7 and 8. In some particular embodiments, s is 2. In still yet further embodiments, x is 2.

In one embodiment, the polyorthoester comprises alternating residues of 3,9-diethyl-3,9-2,4,8,10-tetraoxaspiro[5.5]undecane-3,9-diyl and A:

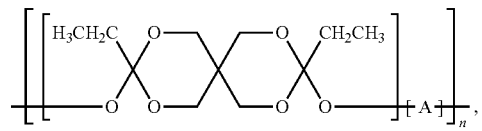

where A is as described above.

In yet one or more additional embodiments, the composition comprising a polyorthoester, an organic acid, and a therapeutically active agent further comprises a solvent. The solvent may be either protic or aprotic in nature.

In yet one or more further embodiments, the therapeutically active agent is solubilized in the composition.

In some embodiments, the composition comprises a polyorthoester, maleic acid, and an amino-amide type local anesthetic.

In another aspect, i.e., a second aspect, provided is a method for inhibiting or impeding the crystallization of an amide- or anilide-type local anesthetic (in its free base form), in a semi-solid formulation comprising a polyorthoester, by adding to the semi-solid formulation, an organic acid such as maleic acid. The addition of the organic acid, e.g., maleic acid, is effective to stabilize the formulation by reducing or eliminating the propensity of the amide- or anilide-type local anesthetic to crystallize in the formulation over time. Preferred organic acids are organic carboxylic acids having two or more proton sources per molecule (i.e., proton donating groups), such as organic di-carboxylic acids or tri-carboxylic acids, or mono-carboxylic acids having an additional acidic proton, such as salicylic acid, a beta-hydroxy mono-carboxylic acid with an additional acidic, phenolic substituent.

In some embodiments of the second aspect, from about 10 mole percent to about 80 mole percent maleic acid is added to the semi-solid formulation relative to the amino-amide type local anesthetic.

In yet an additional aspect, i.e., a third aspect, provided is a method for enhancing/increasing the release rate of a basic, i.e., amino-containing, drug comprised in a polyorthoester formulation by incorporating into the formulation an organic acid. The addition of the organic acid is effective to increase the rate of release of the basic (i.e., alkaline) drug from the polyorthoester formulation over that observed in the absence of the organic acid. More particularly, in one or more embodiments, incorporation of the organic acid is effective to increase the rate of release of the amino-containing drug from the polyorthoester formulation in comparison to a formulation comprising the same components in the same relative amounts but absent the organic acid, when measured either in an in-vitro test at 37° C. over the first 24 hours. Preferably, the incorporation of the organic acid is effective to promote release of a significant portion of the alkaline active agent from the composition, such that 75 weight percent or more, or 80% by weight or more of the drug is released from the composition, either in vitro or in vivo, over a period of up to about 5 days, or up to about 3 days, following administration or initiation of an in vitro drug release experiment (e.g., as described in Example 2), or for a period of about 1 day to about 3 days, or from about 1 day to 5 days, or from about 1 day to 4 days, or from about 2 days to 5 days, or from about 2 days to 4 days, or from about 2 days to 3 days, or from about 3 days to 5 days. Typically, in the absence of the organic acid, the release of the alkaline drug extends over a period of greater than 5 days, such that the period of time required to release at least 75% by weight, or at least 80% by weight or more of the drug is greater, and often significantly greater, than 5 days.

In yet another aspect, i.e., a fourth aspect, provided is a method of treatment, the method comprising dispensing from a needle a composition comprising an amino-containing, alkaline drug, a polyorthoester, and an organic acid, to thereby achieve a controlled release of the alkaline drug from the composition, wherein 75 weight percent or more, or even 80% by weight or more of the drug is released from the composition over a period of about 3 days, about 4 days, or about 5 days.

In one or more embodiments related to the fourth aspect, provided is a method of treatment, the method comprising dispensing from a needle a composition comprising an amino-containing, alkaline drug, a polyorthoester, and an organic acid, to thereby achieve a controlled release of the alkaline drug from the composition, wherein 75 weight percent or more, or even 80% by weight or more of the drug is released from the composition over a period of from 3 to 5 days, e.g. for up to about 5 days, or up to about 3 days, or for a period of about 1 day to about 3 days, or from about 1 day to 5 days, or from about 1 day to 4 days, or from about 2 days to 5 days, or from about 2 days to 4 days, or from about 2 days to 3 days, or from about 3 days to 5 days.

In another aspect, i.e., a fifth aspect, the compositions provided herein are for use in a method of providing local anesthesia to a patient in need thereof. The treatment includes administering to a patient a composition as set forth herein, e.g., comprising an amide or anilide-type local anesthetic, a polyorthoester and an organic acid, to provide a rate of release of anesthetic effective for reducing or preventing pain. Local administration can be, e.g., at a nerve, into the epidural space, intrathecal, or directly to a surgical site or wound. Preferably, 75% or even 80% by weight or more of the drug is released over a period of up to about 5 days.

In some embodiments related to the fourth or fifth aspects, the method comprises dispensing or administering any one or more of the polyorthoester-organic acid-amino-amide type local anesthetic compositions provided herein.

In yet another embodiment, the compositions and delivery systems provided herein are for reducing or treating acute or chronic pain.

For each of the above aspects and embodiments, each aspect or embodiment directed to an active agent is meant to apply to each and every embodiment of the organic acid, and each embodiment of the polyorthoester is meant to apply to each embodiment of an active agent, and each embodiment of an organic acid, as well as combinations and permutations thereof. Additional embodiments of the present systems, compositions and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

Definitions

Figure 1:
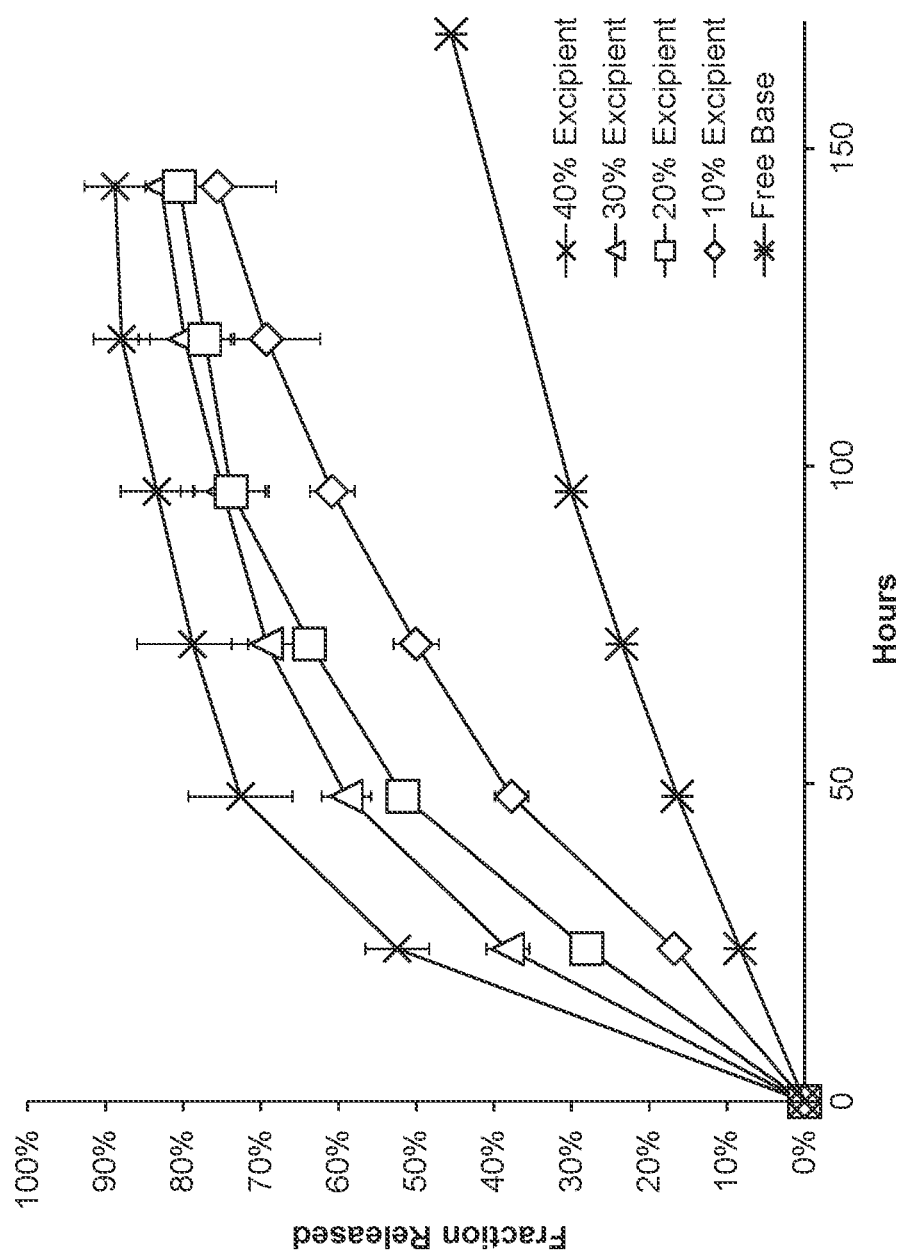
FIG. 1 is a graph that includes plots illustrating the percent of active agent, ropivacaine, released as a function of time, in hours, from a delivery system comprising 5 wt % ropivacaine, 20 wt % polyorthoester, and differing amounts of an exemplary organic carboxylic acid, maleic acid (0 wt % organic acid excipient, bottom plot; 10 mol % organic acid excipient, diamonds; 20 mol % organic acid excipient, squares; 30 mol % organic acid excipient, triangles; 40 mol % organic acid excipient, top plot). See Example 2. The molar amounts of maleic acid are relative to the molar amount of ropivacaine in the formulation. The plots illustrate the ability of the added organic carboxylic acid to significantly increase the amount of basic drug, i.e., ropivacaine, released from the formulation over a time period of 150 hours (over approximately 6 days). Compositions comprising a greater weight percentage of organic acid (and thus mole percent) excipient generally exhibited a faster rate of release of drug for each of the time points measured (as can be seen by a comparison of the slope of each of the plots), and thus had released a greater quantity of drug for each of the time points measured. The compositions exhibited an initial rate of drug release for the first 2 or 3 days following administration that is greater than the rate of drug release over days 4-5 and beyond.

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 10 to 20 weight percent (wt %) is stated, it is intended that 11, 12, 13, 14, 15, 16, 17, 18, and 19 wt % are also explicitly disclosed, as well as the range of values greater than or equal to 10 wt % up to about 20 wt % and the range of values less than or equal to 20 wt % down to about 10 wt %.

"Bioerodible", "bioerodibility" and "biodegradable", which are used interchangeably herein, refer to the degradation, disassembly or digestion of a polymer by action of a biological environment, including the action of living organisms and most notably at physiological pH and temperature. As an example, a principal mechanism for bioerosion of a polyorthoester is hydrolysis of linkages between and within the units of the polyorthoester.

A "polymer susceptible to hydrolysis" such as a polyorthoester refers to a polymer that is capable of degradation, disassembly or digestion through reaction with water molecules. Such a polymer contains hydrolyzable groups in the polymer. Examples of polymers susceptible to hydrolysis may include, but are not limited to, polymers described herein, and those described in U.S. Pat. Nos. 4,079,038, 4,093,709, 4,131,648, 4,138,344, 4,180,646, 4,304,767, 4,957,998, 4,946,931, 5,968,543, 6,613,335, and 8,252,304, and U.S. Patent Publication No. 2007/0265329, which are incorporated by reference in their entirety.

"Molecular mass" in the context of a polymer such as a polyorthoester, refers to the nominal average molecular mass of a polymer, typically determined by size exclusion chromatography, light scattering techniques, or velocity. Molecular weight can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatographic or other liquid chromatographic techniques. Other methods for measuring molecular weight values can also be used, such as the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 3.0, less than about 2.75, less than about 2.25, less than about 1.5, and less than about 1.03.

"Semi-solid" denotes the mechano-physical state of a material that is flowable under moderate stress. A semi-solid material will generally have a viscosity between about 1,000 and 3,000,000 cps (mPa·s) at 37° C., especially between about 1,000 and 50,000 cps (mPa·s) at 37° C. Viscosity may be measured using a Brookfield Viscometer DV-II Pro with a CPA-44PSYZ cup and measured at 37° C. Viscosity measurements of formulations with less than 8,000 cP (mPa·s) are measured at using a CPA-40Z spindle and the system may be verified using 1,000cps silicone oil Brookfield Viscosity Standard. Viscosity measurements for formulations above 8,000 cP (mPa·s) may be evaluated using a CPA-52Z spindle and standardized using the 30,000cps silicone oil Brookfield Viscosity Standard.

An "active agent" or "active ingredient" refers to any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents.

A "small molecule" is a molecule, typically a drug, having a molecular weight of less than about 900 daltons.

A "local anesthetic" is a drug that causes reversible local anesthesia, generally for inducing absence of pain sensation.

The term "amino-amide" class of local anesthetic (also referred to herein as an amide- or anilide local anesthetic) refers to a molecule that functions as a local anesthetic, and contains in its structure both an amino functionality as well as an anilide group, for example, an amide group formed from the amino nitrogen of aniline. These molecules are generally weak bases, with pKb values ranging from about 5.8 to about 6.4.

A "caine" type drug as used herein refers to an amino-amide type local anesthetic, such as bupivacaine, levobupivacaine, ropivacaine, etidocaine, lidocaine, mepivacaine, prilocaine and the like.

"Pharmaceutically acceptable salt" denotes a salt form of a drug having at least one group suitable for salt formation that causes no significant adverse toxicological effects to the patient. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate and phosphate. Suitably pharmaceutically acceptable salt forms are found in, e.g., *Handbook of Pharmaceutical Salts: Properties, Selection and Use*, Weinheim/Zurich:Wiley-VCH/VHCA, 2002; P. H. Stahl and C. G. Wermuth, Eds.

An "organic acid" is an organic molecule having at least one carboxylic acid group that generally possesses a molecular weight that is less than about 300 daltons. An organic acid may have 2 or more carboxylic acid groups, e.g, 2, 3, or 4, carboxylic acid groups. The organic acid may be aliphatic or aromatic, and may optionally contain additional non-basic substituents such as hydroxyl, ester, halo, and the like. Aliphatic organic acids may also contain one or more elements of unsaturation, e.g., a double or a triple bond. Exemplary organic acids include ethanoic acid, propanoic acid, butanoic acid, pentanoic acid, benzoic acid, acetyl salicylic acid, citric acid, fumaric acid, maleic acid, salicylic acid, succinic acid, oxalic acid, malonic acid, glutaric acid, adipic acid, pimelic acid, and so forth.

Mole percent (also designated as mol %) of an organic acid as used herein is relative to the molar amount of the corresponding amino-containing drug. As an example, a composition comprising 100 mmols of an amino-containing drug such as ropivacaine and 10 mmols of an organic acid contains 10 mol percent of the organic acid.

"Polyorthoester-compatible" refers to, in one particular aspect of the properties of the polyorthoester, the properties of an excipient or additive which, when mixed with the polyorthoester, forms a single phase and does not cause any physical or chemical changes to the polyorthoester.

A "therapeutically effective amount" means the amount that, when administered to an animal for treatment of a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e. to a degree of 85% or greater) in reference to the feature or entity.

The term "about", particularly in reference to a given quantity, is meant to encompass deviations of plus or minus five percent.

Additional definitions may also be found in the sections which follow.

Overview

Currently available local anesthetic formulations used to manage post-operative pain generally don't work particularly well after 24 hours—i.e., they are short acting in nature. In exploring the use of semi-solid compositions of amide-type anesthetics such as bupivacaine or ropivacaine (in free base form) for effectively treating and managing pain, problems were encountered. In preparing semi-solid formulations of ropivacaine and bupivacaine (in free base form) with polyorthoesters, it was recognized that the active agent contained within the formulations demonstrated a propensity to crystallize over time (e.g., within about 1 day to about week following formulation preparation). The tendency of the amino-amide "caine" type drugs, when combined with a polyorthoester, to undergo a phase change, results in formulations having decreased stability over time, as well as lower bioavailability, which can ultimately adversely impact the therapeutic efficacy and safety of such formulations. Thus, such formulations were undesirable. In carrying out extensive studies aimed at stabilizing the formulations against crystallization, it was discovered that the addition of an organic acid such as maleic acid to the polyorthoester formulations effectively inhibited the undesirable formation of crystals, thereby unexpectedly stabilizing the formulations. This aspect of the disclosure is described, for example, in Example 9.

In exploring delivery systems of bupivacaine or ropivacaine contained in an exemplary semi-solid polyorthoester delivery vehicle, it was also noted that the formulations demonstrated slow release rates of drug, such that the formulations were generally ineffective for providing release of an amount of drug sufficient for providing effective and extended effective pain relief for a period of up to about 5 days post-administration. See, e.g., Examples 1 and 2 (additional data demonstrating ineffective release of local anesthetic not included herein). In investigating various organic acids for incorporation into the semi-solid polyorthoester delivery vehicle, it was discovered that the organic acids, even when present in very small amounts by weight, were extremely effective in notably improving both the initial release rate, as well as the cumulative release of drug from the formulations. Formulations that had previously been considered unsuitable for providing effective plasma concentrations of drug, e.g., within a time frame of up to about 5 days, e.g., in a time period of about 3 to 5 days post-administration, were thus transformed into desirable, rapid-release formulations by the mere addition of a small amount of organic acid, as will be described in greater detail below.

It was further discovered that by varying the amount of a given organic acid in the formulation, the release rate of the "caine" type drug, e.g., ropivacaine or bupivacaine or the like, could be adjusted to a faster release rate. Formulations having a desirable release profile, e.g., wherein a majority (greater than about 75% by weight, or 80% by weight) of the drug (e.g., caine-type drug) is released in approximately 5 days, were achieved by including in the formulations an effective drug-releasing amount of an organic acid. Formulations comprising only the free base "caine" drug (absent organic acid additive) generally exhibited release of 75-80 wt % or more of drug over a time period of greater, and often significantly greater than about 5 days. Addition of an organic acid, in addition to stabilizing the formulation, accelerated the release such that the release rate of the basic drug was enhanced over the release rate of drug in the same formulation absent the organic acid additive. Formulations and methods which effectively overcome the problems noted above will now be described in greater detail, and are exemplified in Examples 1-9.

Delivery System and Composition

The systems and compositions described herein generally comprise, in addition to a basic active agent, such as an amino-amide type local anesthetic or any small molecule active agent containing an amino functionality, a biodegradable polyorthoester polymer combined with an optional biocompatible organic solvent, and an organic acid. The compositions and systems find use, for example, as drug delivery systems or as medical or surgical devices, e.g., for treatment of pain such as post-operative pain. In the sections which follow, composition components are described.

Polyorthoesters

Although any polyorthoester may be used, polyorthoesters for use in the compositions provided herein are generally composed of alternating residues resulting from reaction of a diketene acetal and a diol, where each adjacent pair of diketene acetal-derived residues is separated by the residue of a reacted diol. The polyorthoester may comprise α-hydroxy acid-containing subunits, i.e., subunits derived from an α-hydroxy acid or a cyclic diester thereof, such as subunits comprising glycolide, lactide, or combinations thereof, i.e., poly(lactide-co-glycolide), including all ratios of lactide to glycolide, e.g., 75:25, 65:35, 50:50, etc. Such subunits are also referred to as latent acid subunits; these latent acid subunits also fall within the more general "diol" classification as used herein, due to their terminal hydroxyl groups. Polyorthoesters can be prepared as described, for example, in U.S. Pat. Nos. 4,549,010 and 5,968,543. Exemplary polyorthoesters suitable for use in the compositions provided herein are described in U.S. Pat. No. 8,252,304.

The mole percentage of α-hydroxy acid containing subunits, $R^1$, generally ranges from 0 to 20 mol % of the total diol components ($R^1$ and $R^3$ as provided below). In one or more embodiments, the mole percentage of α-hydroxy acid containing subunits in the polyorthoester formulation is at least about 0.01 mole percent. Exemplary percentages of α-hydroxy acid containing subunits in the polymer are from about 0 to about 50 mole percent, or from about 0 to about 25 mole percent, or from about 0.05 to about 30 mole percent, or from about 0.1 to about 25 mole percent. For example, in one embodiment, the percentage of α-hydroxy acid containing subunits in the polymer is from about 0 to about 50 mole percent. In another embodiment, the percentage of α-hydroxy acid containing subunits in the polymer is from about 0 to about 25 mole percent. In yet another particular embodiment, the percentage of α-hydroxy acid containing subunits in the polymer is from about 0.05 to about 30 mole percent. In yet another embodiment, the percentage of α-hydroxy acid containing subunits in the polymer is from about 0.1 to about 25 mole percent. As an illustration, the percentage of α-hydroxy acid containing subunits may be 0, 1, 2, 3, 4, 5, 6, 7, 8, 9, 10, 11, 12, 13, 14, 15, 16, 17, 18, 19, 20, 21, 22, 23, 24, 24, 26, 27, 28, 29 or 30 mole percent, including any and all ranges lying therein, formed by combination of any one lower mole percentage number with any higher mole percentage number.

More particularly, a poly(orthoester) for use in the compositions and delivery systems provided herein is described by the following formula:

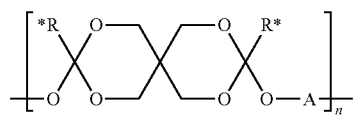

III where: $R^*$ is a $C_{1-4}$ alkyl (e.g., C1, C2, C3 or C4 alkyl), n is an integer ranging from 5 to 400, and A in each subunit is $R^1$ or $R^3$. That is, in any monomer unit

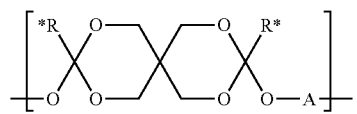

of the polymer of Formula III, A may be either $R^1$ or $R^3$.

In a particular embodiment, $R^*$ is ethyl (i.e., C2 alkyl). A subunit in accordance with formula III, wherein $R^*$ is ethyl, corresponds to a subunit resulting from reaction of a diol as provided herein with 3,9-di(ethylidene)-2,4,8,10-tetraoxaspiro[5.5]undecane (DETOSU), a diketene acetal having the structure:

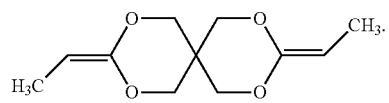

In reference to Formula III, as described previously, A may correspond to $R^1$. $R^1$ is

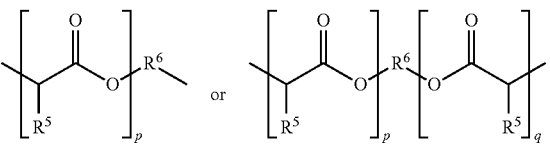

where p and q are each independently integers that range from between about 1 to 20 (e.g., are each independently selected from 1, 2, 3, 4, 5, 6, 7, 8, 9, 10, 11, 12, 13, 14, 15, 16, 17, 18, 19, and 20), each $R^5$ is independently hydrogen or $C_{1-4}$ alkyl (e.g., is H, or C1, C2, C3, or C4 alkyl); and $R^6$ is:

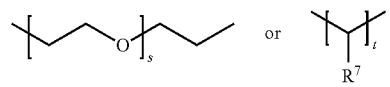

where s is an integer from 0 to 10 (e.g., is selected from, 0, 1, 2, 3, 4, 5, 6, 7, 8, 9, 10); t is an integer from 2 to 30; and $R^7$ is hydrogen or $C_{1-4}$ alkyl (e.g., is H or C1, C2, C3, or C4 alkyl). In one or more particular embodiments, $R^7$ is H. The $R^1$ subunits are (x-hydroxy acid-containing subunits, i.e., subunits derived from an (x-hydroxy acid or a cyclic diester thereof.

In reference to Formula III, A may also correspond to $R^3$, where $R^3$ is:

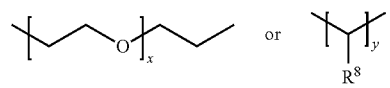

and x is an integer ranging from 1 to 100, and is, in certain particular instances, selected from 1, 2, 3, 4, and 5; y is an integer in a range from 2 to 30; and $R^8$ is hydrogen or $C_{1-4}$ alkyl (C1, C2, C3 or C4 alkyl).

In a particular embodiment, $R^8$ is H.

In some embodiments, the poly(orthoester) is one in which A is $R^1$ or $R^3$, where $R^1$ is

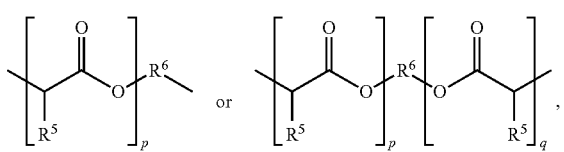

where p and q are each independently integers that range from between about 1 and 20, where the average number of p or the average number of the sum of p and q (p+q) is between about 1 and 7 (e.g., 1, 2, 3, 4, 5, 6, 7) when R1 is present in the poly(orthoester) polymer; x and s are each independently an integer ranging from 0 to 10; and t and y are each independently an integer ranging from 2 to 30. In one or more particular embodiments, $R^5$ is H.

One particular polyorthoester (of formula III), comprises 80% triethylene glycol (TEG) and 20% TEG-glycolide (comprising on average 2 glycolides per subunit, i.e., TEG-diglycolide).

Additional particular poly(orthoesters) are those in which A is $R^1$ or $R^3$, where $R^1$ is

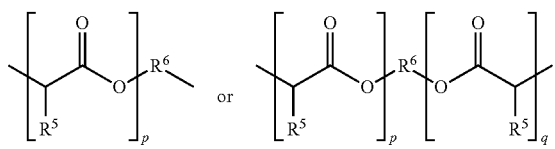

and p and q are each independently integers that vary from between about 1 and 20, or between about 1 and 15, or between about 1 and 10, where the average number of p or the average number of the sum of p and q (i.e., p+q) is between about 1 and 7 when R1 is present in the poly(orthoester) polymer. Additionally, particular ranges of x and s (in reference to the particular embodiment above or in reference to any polyorthoester as provided herein) are those in which each is independently an integer ranging from 0 to 7 or from 1 to 5. Similarly, particular ranges for t and y are those in which each independently varies from 2 to 10.

Particular polyorthoesters are those in which $R^5$ is hydrogen or methyl.

In certain embodiments, s and x are each independently selected from 1, 2, 3, 4, 5, 6, 7 and 8. In some embodiments, s is 2. In some other embodiments, x is 2.

An exemplary polyorthoester comprises alternating residues of 3,9-diethyl-3,9-2,4,8,10-tetraoxaspiro[5.5]undecane-3,9-diyl and A:

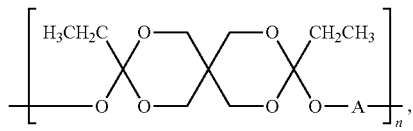

where A is as described above.

Polyorthoesters such as those described herein can be prepared by reacting an illustrative diketene acetal, 3,9-di(ethylidene)-2,4,8,10-tetraoxaspiro[5.5]undecane (DETOSU),

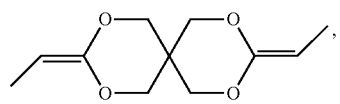

with one or more diols as described above, such as HO—$R^1$—OH or HO—$R^3$—OH. Illustrative diols include oligoethylene glycols such as triethylene glycol (TEG), oligoethylene glycols modified at one or both termini with an (α-hydroxy acid such as an oligoethylene glycol diglycolide or an oligoethylene glycol dilactide, organic diols having a hydrocarbyl core of from 2 to 30 carbon atoms such as 1,6-hexanediol, 1,10-decanediol, cis/trans 1,4-cyclohexane dimethanol, para-menthane-3,8-diol, 1,4-butanediol, 1,5-pentanediol, 1,7-heptanediol, 1,8-octanediol, 1,10-decanediol, 1,12-dodecanediol, and cyclic equivalents thereof, where the hydroxyl groups can be at any two positions within the cycloalkyl or alkylene ring. An organic diol can possess from 2 to 20 carbon atoms. The organic diol can be linear, branched or cyclic, and may also be saturated or unsaturated. Generally, unsaturated diols will possess from 1-3 elements of unsaturation. A particular poly(orthoester) will contain from about from 10 to 50 total mole percent of subunits derived from one or more organic diols having a hydrocarbyl core.

Diols such as HO—$R^1$—OH are prepared as described in U.S. Pat. No. 5,968,543 and in Heller et al., *J. Polymer Sci., Polymer Letters Ed.* 18:293-297 (1980). For example, a diol of the formula HO—$R^1$—OH comprising a polyester moiety can be prepared by reacting a diol of the formula HO—$R^3$—OH with between 0.5 and 10 molar equivalents of a cyclic diester of an (α-hydroxy acid such as lactide or glycolide, and allowing the reaction to proceed at 100-200° C. for about 12 hours to about 48 hours. Suitable solvents for the reaction include organic solvents such as dimethylacetamide, dimethyl sulfoxide, dimethylformamide, acetonitrile, pyrrolidone, tetrahydrofuran, and methylbutyl ether. Although the diol product is generally referred to herein as a discrete and simplified entity, e.g., TEG diglycolide (and diol reaction products such as TEG diglycolide), it will be understood by those of skill in the art that due to the reactive nature of the reactants, e.g., ring opening of the glycolide, the diol is actually a complex mixture resulting from the reaction, such that the term, TEG diglycolide (or any other term referring a similar product), generally refers to the average or overall nature of the product.

A particular polyorthoester is prepared by reacting 3,9-di(ethylidene)-2,4,8,10-tetraoxaspiro[5.5]undecane (DETOSU) with one or more reactive diols. Generally, the polyorthoester is prepared by reacting DETOSU with two or more reactive diols under anhydrous conditions. A particularly suitable polyorthoester is prepared by reacting DETOSU with triethylene glycol and triethylene glycol diglycolide as described in U.S. Pat. No. 8,252,305. A particular polyorthoester prepared from DETOSU-triethylene glycol-triethylene glycol diglycolide possesses the following molar ratios of components: 90:80:20, although the relative ratios of components can be suitably varied as described above.

A polyorthoester formed by the reaction of DETOSU with TEG and TEG diglycolide can generally be described as possessing the following subunits, where $R^1$ corresponds to the diolate portion derived from triethylene glycol diglycolide (formed by reaction of glycolide with TEG) and $R^3$ corresponds to the diolate portion derived from triethylene glycol:

where A is $R^1$, and $R^1$ is

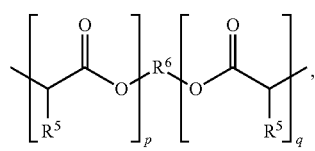

where $R^5$ is H and $R^6$ is

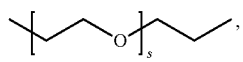

the resulting component of the polyorthoester is:

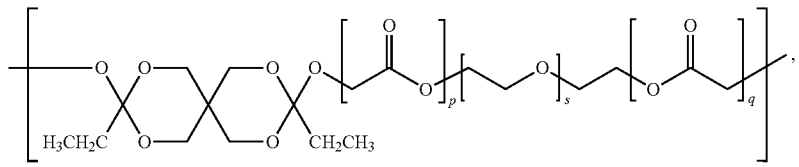

where the sum of p and q is, on average, 2 and s is 2; and when A is $R^3$, and $R^3$ is

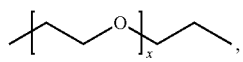

where x is 2, the resulting subunit or component of the polyorthoester is.

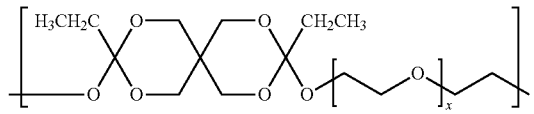

Structures corresponding to polyorthoesters prepared from the various α-hydroxy acid-containing subunits and additional diols described herein can be readily envisioned.

Exemplary polyorthoesters possess a weight average molecular weight of about 1000 Da to about 200,000 Da, for example from about 2,500 Da to about 100,000 Da or from about 3,500 Da to about 20,000 Da or from about 4,000 Da to about 10,000 Da or from about 5,000 Da to about 8,000 Da. Illustrative molecular weights, in Da, are 2500, 5000, 5500, 6000, 6500, 7000, 7500, 8000, 8500, 9000, 9500, 10,000, 20,000, 30,000, 40,000, 50,000, 60,000, 70,000, 80,000, 90,000, 100,000, 120,000, 150,000, 175,000 and 200,000, and ranges therein, wherein exemplary ranges include those formed by combining any one lower molecular weight as described above with any one higher molecular weight as provided above, relative to the selected lower molecular weight.

In one particular embodiment related to the polyorthoester in the delivery system, the polyorthoester has a molecular weight ranging from about 2,500 daltons to 10,000 daltons.

In one embodiment, the poly(orthoesters) described in this section are semi-solids both at room temperature and at temperatures above room temperature. In one embodiment, polyorthoesters containing 80 to 100 mole % $R^3$, where $R^3$ is

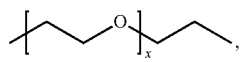

where x is 2, are semisolid polymers at both room temperature and at temperatures above room temperature. Semisolid polymers exist either in a glassy or viscous liquid state. Semisolid polymers typically display a glass transition temperature (Tg) below room temperature. Below the Tg, semisolid polymers can be considered to exist in a glassy state, while above the Tg, the polyorthoester can be considered to exist in a liquid state. Semisolid polyorthoester polymers are not thermoplastic polymers.

Generally, the compositions and delivery systems provided herein are comprised of a polyorthoester of formula I, formula II, formula III or formula IV:

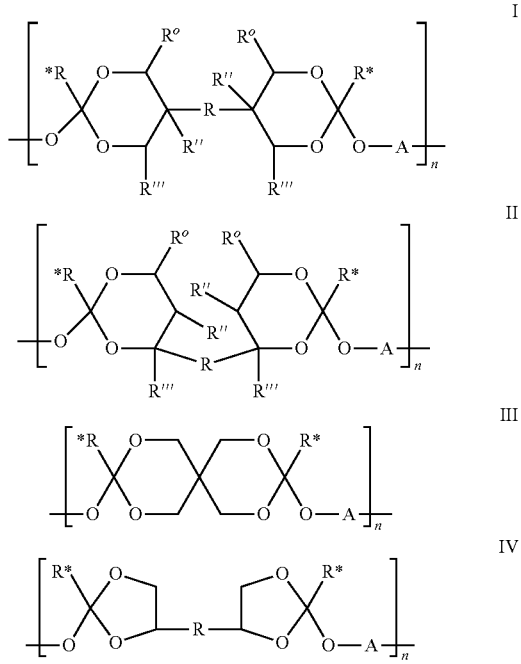

where in reference to Formulas I-IV:
R is a bond, —$(CH_2)_a$—, or —$(CH_2)_b$—O—$(CH_2)_c$—;
where a is an integer of 1 to 12 (e.g., selected from 1, 2, 3, 4, 5, 6, 7, 8, 9, 10, 11, and 12), or from 1 to 10, and b and c are independently integers from 1 to 5 (e.g., selected from 1, 2, 3, 4, and 5);
R* is a $C_{1-4}$ alkyl;
$R^o$, R" and R"' are each independently H or $C_{1-4}$ alkyl;
n is an integer of at least 5; and
A is a diol.

For example, the compositions and delivery systems described herein may be comprised of a polyorthoester of Formula I, Formula II, Formula III or Formula IV, where:
R is a bond, —$(CH_2)_a$—, or —$(CH_2)_b$—O—$(CH_2)_c$—;
where a is an integer of 1 to 12, or from 1 to 10, and b and c are independently integers of 1 to 5;
R* is a $C_{1-4}$ alkyl;
$R^o$, R" and R"' are each independently H or $C_{1-4}$ alkyl;

n is an integer of at least 5; and

A is $R^1$, $R^2$, $R^3$, or $R^4$, where $R^1$ is an α-hydroxy acid containing subunit as described in the preceding paragraphs, e.g.,

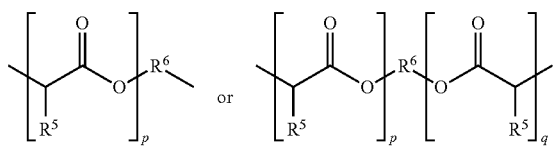

where:

p and q are integers that vary from between about 1 and 20, or between about 1 and 15, or between about 1 and 10, where the average number of p or the average of the sum of p and q (i.e., p+q) is between about 1 and 7 when $R^1$ is present in the poly(orthoester) polymer; $R^5$ is hydrogen or $C_{1-4}$ alkyl (e.g., methyl, ethyl, propyl, butyl, isopropyl, isobutyl, sec-butyl); and $R^6$ is selected from the group consisting of

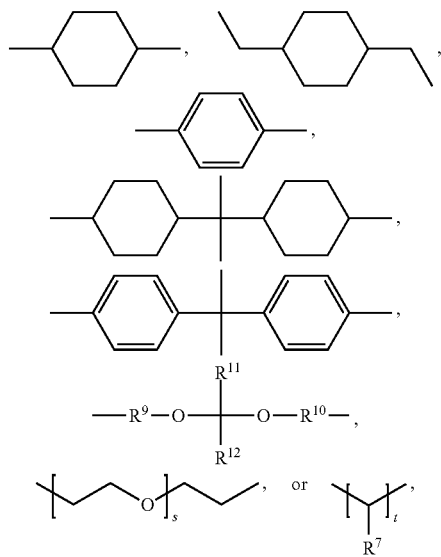

where:

s is an integer of 0 to 30, or more particularly from 0 to 10;

t is an integer of 2 to 200, and more particularly from 2 to 30; and $R^7$ is hydrogen or $C_{1-4}$ alkyl;

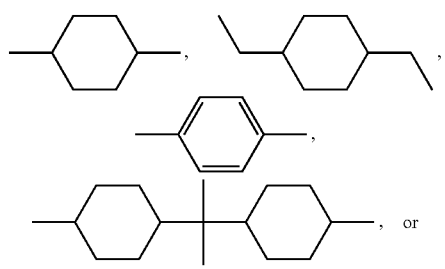

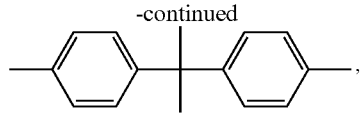

$R^2$ is:
$R^3$ is:

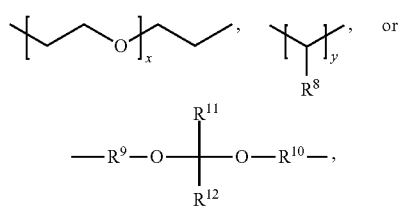

where:

x is an integer ranging from 0 to 200, or from 0 to 100;

y is an integer ranging from 2 to 200, or more particularly from 2 to 30;

$R^8$ is hydrogen or $C_{1-4}$ alkyl;

$R^9$ and $R^{10}$ are independently C1-12 alkylene;

$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and $R^4$ is the residue of a diol containing at least one functional group independently selected from amide, imide, urea, and urethane groups.

In certain instances, the polyorthoester is one in which A is $R^1$, $R^3$, or $R^4$, where $R^1$ is:

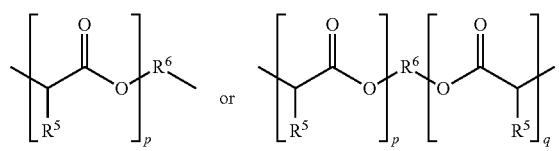

where:

p and q are integers that vary from between about 1 to 20 and the average number of p or the average of the sum of p and q is between 1 and 7 when $R^1$ is present in the poly(orthoester) polymer; $R^3$ and $R^6$ are each independently:

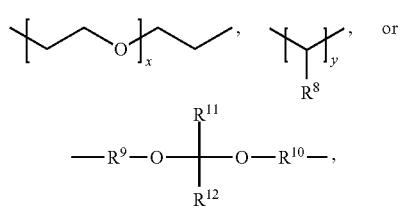

where:

x is an integer of 0 to 30;

y is an integer of 2 to 200;

$R^8$ is hydrogen or $C_{1-4}$ alkyl;

$R^9$ and $R^{10}$ are independently $C_{1-12}$ alkylene;

$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and $R^4$ is a residual of a diol containing at least one functional group independently selected from amide, imide, urea and urethane groups; and $R^5$ is hydrogen or $C_{1-4}$ alkyl.

In one particular embodiment of the polyorthoester, the fraction of the A units that are of the formula $R^1$ is between 5 and 15 mole percent.

One exemplary polyorthoester is that of formula I, II, III, or IV, or more particularly, of Formula III, where:
none of the units have A equal to $R^2$;
$R^3$ is:

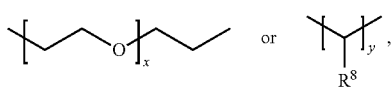 or 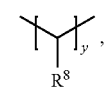, where:
x is an integer of 1 to 100, or from 0 to 10;
y is an integer of 2 to 30; and
$R^6$ is:

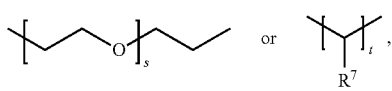 or 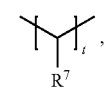, where:
s is an integer of 1 to 10, or from 0 to 10;
t is an integer of 2 to 30; and
$R^5$, $R^7$, and $R^8$ are independently hydrogen or methyl.

An additional representative polyorthoester of Formula I, II, III or IV, and in particular, of Formula III, is one in which $R^3$ and $R^6$ are both —(CH$_2$—CH$_2$—O)$_2$—(CH$_2$—CH$_2$)—; $R^5$ is methyl; and where p and q are each independently selected from 1, 2, 3, 4, 5, 6, 7, 8, 9, 10, 11, 12, 13, 14, 15, 16, 17, 18, 19, and 20, for example, p can be 1 or 2.

In another embodiment of a polyorthoester of Formula I, II, III or IV, or more particularly, of Formula III, $R^3$ and $R^6$ are both —(CH$_2$—CH$_2$—O)$_2$—(CH$_2$—CH$_2$)—; $R^5$ is methyl; and p or the sum of p and q is on average 2.

In another variation, the polyorthoester is of formula I, II, III or IV, or is of formula III, R is —(CH$_2$)$_b$—O—(CH$_2$)$_c$—; where b and c are both 2; R* is a C2 alkyl.

Additional representative polyorthoesters are those of Formula I, II, III or IV, or in particular, of Formula III, in which $R^5$ is hydrogen or methyl; $R^6$ is

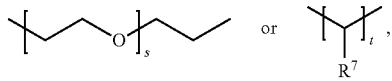 or 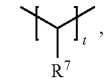, where s is an integer from 0 to 10, e.g., preferably selected from 1, 2, 3, or 4; t is an integer from 2 to 30, particularly selected from 2, 3, 4, 5, 6, 7, 8, 9 and 10; $R^7$ is hydrogen or methyl; and $R^3$ is

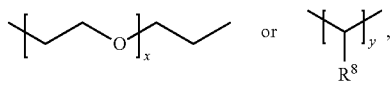 or 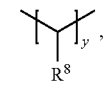, where x is an integer from 0 to 10, e.g., preferably selected from 1, 2, 3, or 4; y is an integer from 2 to 30, particularly selected from 2, 3, 4, 5, 6, 7, 8, 9 and 10; $R^8$ is hydrogen or methyl; $R^4$ is selected from a residue of an aliphatic diol having from 2-20 carbon atoms (e.g., selected from 2, 3, 4, 5, 6, 7, 8, 9, 10, 11, 12, 13, 14, 15, 16, 17, 18, 19, and 20 carbon atoms), preferably having from 2 to 10 carbon atoms, interrupted by one or two amide, imide, urea, or urethane groups. In some cases, the proportion of subunits in the polyorthoester in which A is $R^1$ is from about 0.01-50 mole percent. In certain instances, the proportion of subunits in the polyorthoester in which A is $R^1$ is from about 0.05 to about 30 mole percent, or from about 0.1 to 25 mole percent. Illustrative mole percentages include 10, 15, 20 and 25 mole percent of subunits in the polyorthoester in which A is $R^1$. In one embodiment, the mole percent is 20. Additionally, in one or more further embodiments, the proportion of subunits in which A is $R^2$ is less than about 20 percent, or less than about 10 percent, and may be even less than about 5 percent, and the proportion of subunits in which A is $R^4$ is less than 20 percent, or is less than about 10 percent, and in some instances, is less than 5 percent.

The polyorthoester, as shown in Formula I, Formula II, Formula III and Formula IV, in certain embodiments, is one of alternating residues of a diketene acetal and a diol, with each adjacent pair of diketene acetal residues being separated by the residue of one polyol, such as a diol. In one or more particular embodiments, the polyorthoester is that of Formula III.

One illustrative polyorthoester is prepared from DETOSU:TEG:TEG-diGL, at a molar ratio of 90:80:20.

Polyorthoesters having a higher mole percentage of the "α-hydroxy acid containing" units possess a higher rate of bioerodibility. Particular polyorthoesters are those in which the mole percentage of α-hydroxy acid containing subunits is at least about 0.01 mole percent. Exemplary percentages of α-hydroxy acid containing subunits in the polymer are from about 0.01 to about 50 mole percent, preferably from about 0.05 to about 30 mole percent, from about 0.1 to about 25 mole percent. As an illustration, the percentage of α-hydroxy acid containing subunits may be 1, 2, 3, 4, 5, 6, 7, 8, 9, 10, 11, 12, 13, 14, 15, 16, 17, 18, 19, 20, 21, 22, 23, 24, 24, 26, 27, 28, 29 or 30 mole percent, including any and all ranges lying therein, formed by combination of any one lower mole percentage number with any higher mole percentage number. The mole percentage of the "α-hydroxy acid containing" units appropriate to achieve a desired composition will vary from formulation to formulation.

The amount of the polyorthoester in the composition generally ranges from about 1% to about 99% by weight. Illustrative amounts of polyorthoester in the composition are from about 5% to about 90% by weight, or from about 10% to about 90% by weight, or from about 20% to about 90% by weight, or from about 30% to about 85% by weight, or from about 40% to about 85% by weight.

Exemplary polyorthoesters possess a molecular weight of about 1,000 Da to 20,000 Da, for example from 1,000 Da to 10,000 Da or preferably from 1,000 Da to 8,000 Da, or from about 1,500 Da to about 7,000 Da.

As an example, an illustrative polyorthoester may be prepared by reaction of a diketene acetal according to one of the following formulas:

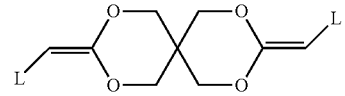

-continued

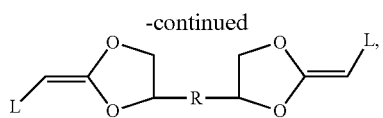

where L is hydrogen or a $C_{1-3}$ alkyl, and R is as defined above, with a diol according to formula HO—$R^1$—OH and at least one diol according to the formulae, HO—$R^2$—OH, HO—$R^3$—OH, or HO—$R^4$—OH (where $R^1$, $R^2$, $R^3$ and $R^4$ are as described above). In the presence of water, the α-hydroxy acid containing subunits are readily hydrolyzed at body temperature and at physiological pH to produce the corresponding hydroxyacids, which can then act as catalysts to control the hydrolysis rate of the polyorthoester without the addition of exogenous acid. Thus, as described previously, polyorthoesters having a higher mole percentage of α-hydroxy acid-containing subunits possess a higher degree of bioerodibility.

Methods of manufacturing the polyorthoesters are well known in the art, and are described, e.g., in U.S. Pat. Nos. 6,613,355 and 8,252,304.

Organic Acids

The composition comprises an organic acid. As described previously, the incorporation of one or more organic acids in the formulation is effective to facilitate the release of an amino-containing, basic small molecule drug, in particular, during the early stages of delivery (e.g., days 1-3 post-administration or dissolution). The organic acid, e.g., maleic acid, is also effective, in the instance of a polyorthoester formulation comprising a "caine" amino-amide type local anesthetic, to prevent or reduce the tendency of the active agent comprised within the formulation to undergo a phase change over time, i.e., to crystallize.

Generally, the organic acid is a carboxylic acid. Most suitable are organic acids having a molecular weight less than about 300 daltons. The organic acid may contain one, two or more carboxylic acid groups. For example, an organic acid may have e.g., 1, 2, 3, or 4 carboxylic acid groups. For example, the organic acid may be a C2-C12, typically a C2-C8, aliphatic, unsubstituted or substituted, saturated straight-chain mono-, di-, or tri-carboxylic acid. Alternatively, the organic acid may be a C2-C12, typically a C2-C8 aliphatic, unsubstituted or substituted, mono, di-, or tri-carboxylic acid containing one or more elements of unsaturation (e.g., one or more double or triple bonds). The organic acid may also be an aromatic mono, di- or tri-carboxylic acid, having from about 7 to 14 carbon atoms.

The organic acid, which can be aliphatic or aromatic, may optionally contain one or more additional non-basic substituents such as hydroxyl (e.g., citric acid), ester (e.g., acetylsalicyclic acid), ether, thioether, halo, or the like, so long as the substituents are non-reactive with the formulation components on a practical time scale and under typical storage conditions, and have no adverse effect on the polyorthoester-basic drug formulation. The organic acid may be a linear or branched hydrocarbon; aliphatic organic acids may also contain one or more elements of unsaturation, e.g., a double or a triple bond, such as fumaric or maleic acid.

In some embodiments, the organic acid is a mono-carboxylic acid. Exemplary mono-organic acids include ethanoic acid, propanoic acid, butanoic acid, pentanoic acid, hexanoic acid, heptanoic acid, and the like.

In some further embodiments, the organic acid is an aromatic organic acid. Aromatic mono-carboxylic acids include benzoic acid, salicylic acid and acetyl salicylic acid. Salicylic acid possesses a weakly acidic hydroxyl substituent on the phenyl ring, ortho to the carboxylic acid function, thereby making this organic acid function somewhat more like a di-acid.

Also suitable for use in the formulation is a di-carboxylic-acid. Unsaturated di-acids suitable for use include fumaric acid and maleic acid, both butenedioic acids, where fumaric acid is the trans-isomer, while maleic acid is the cis isomer. Additional alkene-dioic or alkane dioic acids may also be employed. Additional di-carboxylic acids, e.g., C2-C7 alkane dioic acids suitable for use include oxalic acid, malonic acid, succinic acid, glutaric acid, adipic acid, pimelic acid, and so forth. Maleic acid is a particularly useful organic acid.

Additional representative organic acids include tri-acids such as a C2-C12, or more typically a C2-C8, tri-carboxylic acid. An illustrative tri-acid is citric acid, which also contains a hydroxyl function at the 3-carbon position.

In certain formulations, organic acids having more than one carboxylic acid functionality, or an additional proton-donor in the molecule, such as in the case of salicylic acid, are preferred. Such di-acids, tri-acids, and mono-acids having an additional proton source are particularly useful since less organic acid additive is required, on a per mole (or even a per weight) basis, to achieve a beneficial effect due to the greater number of proton-donor groups in the organic acid molecule when compared to an organic acid having a fewer number of carboxylic acid/proton donating groups.

Generally, the formulation comprises from about 1 mole percent to about 95 mole percent of an organic acid relative to the therapeutic agent such as an amino-amide local anesthetic. More typically, the composition comprises 10-80 mole percent of a mono-carboxylic acid, or from about 10-40 mole percent of a di-carboxylic acid, or from about 10 to 25 mole percent of a tri-carboxylic acid. Typically, the organic acid is present in less than an equimolar amount when compared to the amino-amide anesthetic, such that the therapeutic agent is present as a mixed salt-base. Generally, due to the low molecular weight of the organic acid excipient, the composition comprises a small quantity by weight of the organic acid. Illustrative weight percentages of the organic acid are from about 0.01 wt % to about 5 wt %, or from about 0.01 wt % to about 3 wt %, or from about 01. wt % to about 2 wt %, or from about 0.1 wt % to about 1 wt %. Illustrative weight percentages of the organic acid are 0.01 wt %, 0.02 wt %, 0.03 wt %, 0.04 wt %, 0.05 wt %, 0.06 wt %, 0.07 wt %, 0.08 wt %, 0.09 wt %, 0.10 wt %, 0.15 wt %, 0.20 wt %, 0.25 wt %, 0.30 wt %, 0.35 wt %, 0.40 wt %, 0.45 wt %, 0.50 wt %, 0.55 wt %, 0.60 wt %, 0.65 wt %, 0.70 wt %, 0.75 wt %, 0.80 wt %, 0.85 wt %, 0.90 wt %, 0.95 wt %, 1 wt %, 1.5 wt %, 2.0 wt %, 2.5 wt %, 3 wt %, 3.5 wt %, 4 wt %, 4.5 wt %, 5.0 wt %, including all ranges between any two of the foregoing weight percentages. The amount of the organic acid additive comprised in the formulation will depend, at least in part, upon the identity of the particular active agent, the amount of active agent contained in the formulation, the particular polyorthoester, amount thereof, and desired delivery profile.

The presence of the organic acid, i.e., maleic acid, is effective, e.g., in the case of an amide-anilide local anesthetic provided in a polyorthoester polymer matrix, to stabilize the formulation against crystallization over time. See, e.g., Example 9.

The Applicants further discovered that by varying the amount of a given organic acid in the formulations, the release rate of the "caine" type drug, e.g., ropivacaine or bupivacaine or of any basic small molecule drug in its free base form, can be adjusted to a faster release rate. Generally speaking, for a given organic acid, formulations comprising a greater amount of organic acid exhibited a faster release rate which was generally most pronounced during the first 1-3 days post administration. Formulations absent an organic acid generally released the basic active agent over an extended period of time, e.g., greater than 5 days. However, upon addition of an effective drug-releasing amount of an organic acid, formulations having a desirable rapid release profile, e.g., wherein a majority (>75 wt % or 80 wt %) of the drug (e.g., caine-type or basic drug) is released in approximately 5 days, were attained. As can be seen from the examples provided herein, the rate of release of drug from the instant formulations (e.g., faster or slower) can be tailored by adjusting the amount of organic acid contained in the semi-solid polyorthoester-amino-amide anesthetic formulation.

Thus, the unforeseen advantages of inclusion of an organic acid into the instant formulations is two-fold. That is to say, in addition to stabilizing the formulation against crystallization of a caine-type anesthetic, the incorporation of an organic acid was found to accelerate the rate of release such that the release rate of the basic drug was significantly enhanced over the release rate of drug in the same formulation absent the organic acid additive.

Illustrative compositions demonstrating the beneficial influence of the addition of a small amount of an illustrative organic acid such as maleic acid are described in Examples 1-5 and 9.

Ropivacaine formulations containing approximately 5 weight percent drug in a representative polyorthoester delivery vehicle are described in Example 1. The samples were evaluated both in vitro and in vivo as described in Examples 2 and 3, respectively. The formulations contained from 0% maleic acid to 40 mol percent maleic acid relative to the active agent (from 0.2 to 0.8 weight percent organic acid). In-vitro release profiles for the formulations are shown in FIG. 1. The graphs in FIG. 1 illustrate the ability of a small amount of added organic carboxylic acid (i.e., less than 1% by weight) to significantly increase the amount of basic drug, i.e., ropivacaine, released from the formulation, i.e, to transform the formulation from a non-rapid release formulation into a rapid release formulation. Compositions comprising a greater weight percent of organic acid excipient generally exhibited a faster rate of release of drug for each of the time points measured (as can be seen by a comparison of the slope of each of the plots), and thus had released a greater quantity of drug at each of the time points measured. The compositions exhibited a rate of drug release for the first 2 or 3 days following administration that was faster than the rate of drug release over days 4-5 and beyond. This is particularly beneficial for formulations for treating pain (i.e., providing a therapeutic level of pain relief within the first 24-hours post administration. Ideally, the instant formulations will release from about 30-40 weight percent of active agent over about the first 24-hours post-administration. Thus, addition of an organic acid, optimally at a molar percentage relative to the amino-containing drug, i.e., a 'caine' type drug, of less than 100 mol %, e.g., from about 1 mole percent to about 95 mole percent, or from about 5 mole percent to about 85 mole percent, or from about 10 mol percent to 80 mol percent, to polyorthoester formulations such as provided herein, is effective to enhance the release of drug from the formulation to thereby provide a formulation that is effective to release at least about approximately 75 wt % of drug from the formulation in 5 days or fewer, e.g., in from 1-5 days, when evaluated by an in-vitro test method as described in Example 2, or upon in-vivo administration.

As shown in FIG. 1, at approximately 48 hours, only about 16% ropivacaine had been released from the composition that did not contain organic acid, while in contrast, at the same 48 hour time point, compositions containing 10 mol %, 20 mol %, 30 mol % and 40 mol % organic acid had released approximately 38%, 52%, 59% and 73% ropivacaine, respectively. As can be seen, the initial release of drug was improved in a striking manner by the addition of a small amount of organic acid, e.g., from 10 mol % to 40 mol % of the di-acid, maleic acid. At 96 hours following initiation of the in-vitro release test, the formulation without organic acid had released only 30 wt % ropivacaine, while in contrast, the formulation containing 40 mol % organic acid had released approximately 83% ropivacaine. In essence, these results demonstrate the transformation of a non-rapid release ropivacaine-polyorthoester formulation unsuitable for providing effective and sustained pain relief over a period of up to 5 days (Composition 000) to a rapid-release formulation suitable for reducing or preventing pain by the addition of a small quantity of an organic acid such as maleic acid. The data shown in FIG. 1 is provided in Table 2A in tabular form.

Figure 2:
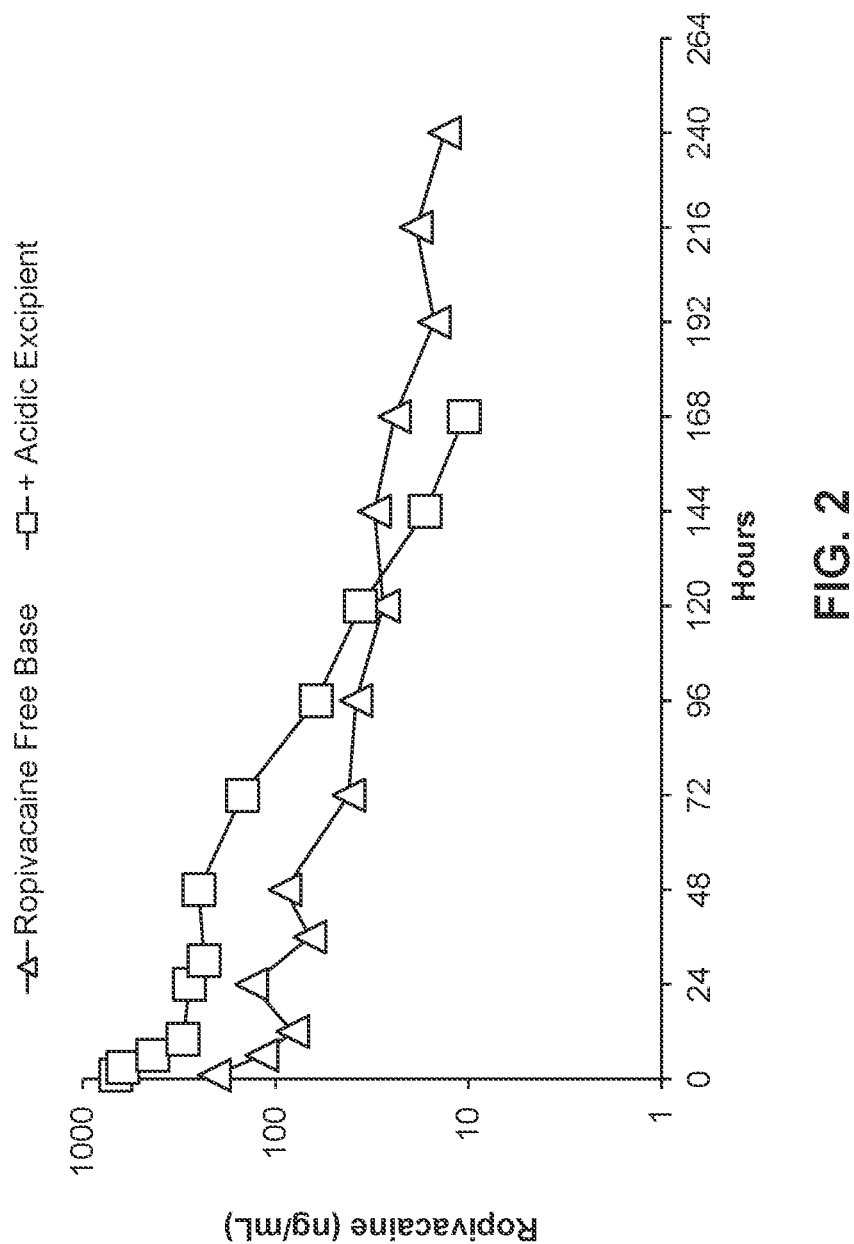
FIG. 2 is a graph illustrating the pharmacokinetic (PK) data for exemplary polyorthoester-ropivacaine formulations with and without added organic acid excipient, where concentration of ropivacaine in ng/mL is provided on the x-axis versus time, in hours, on the y-axis. The pharmacokinetic data is consistent with the in vitro data and illustrates increased concentrations of the active agent, ropivacaine, up to about 120 hours for the organic acid-comprising formulation when compared to the formulation absent the organic acid excipient, consistent with increased release of drug from the organic-acid excipient comprising-formulation.

Example 3 describes an in-vivo canine study designed to explore the pharmacokinetics of the polyorthoester-ropivacaine formulations both with (30 mol percent) and without added organic acid excipient. Plasma samples were analysed by LC/MS/MS (liquid chromatography/tandem mass spectrometry) to determine concentrations of ropivacaine. LC/MS/MS is suitable for determining the plasma concentration of the amino-amide type local anesthetic when administered in vivo in a formulation as provided herein. While both formulations provided measurable plasma concentrations of ropivacaine for at least 5 days following administration, the formulation containing the added organic acid released drug faster than the formulation with the free base alone, as indicated by higher plasma levels of drug at all time points up to 120 hours post-administration. The pharmacokinetic data is consistent with the in vitro data and illustrates increased concentrations of the active agent, ropivacaine, detected in plasma up to about 120 hours post-administration for the organic acid-comprising formulation when compared to the formulation absent the organic acid excipient, consistent with the increased release rate of drug from the organic-acid excipient comprising-formulation as described in Example 2. The data shown in FIG. 2 is provided in Table 2-B.

This data from Example 3 further illustrates that the incorporation of even small amounts of an organic acid such as maleic acid, in this case, 0.6 weight percent of the polyorthoester formulation, can notably impact the release of amino-containing active agent from the formulation, particularly at the early stages post-administration. At the 1 hour time point, plasma levels of drug were 3-fold higher than for the formulation that did not contain organic acid. At 6 hours post-administration, plasma drug levels were 3.7 times higher for the organic acid-containing formulation, while at 24 hours, plasma drug levels were approximately twice as high. This trend continued with plasma drug levels 2.8 times greater for the organic acid containing formulation at 48 hours, and 3.6 times greater at 72 hours. A striking difference in the release profile of the polyorthoester formulation can thereby be attained by the addition of organic acid. This effect is particularly advantageous for drugs such as local anesthetics that are often applied locally, for example, at a wound or incision site, for the treatment of pain.

Similar results were obtained for polyorthoester-based bupivacaine delivery systems as described in Example 4. The illustrative polyorthoester-based bupivacaine delivery systems comprised from 5 to 15 wt % bupivacaine and from 0.8 wt % to 1.7 wt % maleic acid (from 16.5 mol % to 40 mol %). In vitro release of bupivacaine form the formulations is described in Example 5, with accompanying data summarized in Table 4. As can be seen from the results in Table 4, the cumulative amount of bupivacaine released from the formulations at each time point was the greatest for the formulation containing the greatest amount of organic acid (Composition 102). At the 24 hour time point, over 2 times the quantity of bupivacaine had been released from formulation 102 relative to formulation 101, where formulation 102 contained about 1.7 times more maleic acid than formula 101. At the 24 hour time point, about 1.7 times the amount of bupivacaine had been released from formulation 103 relative to formulation 101, where formulation 103 contained about 1.6 times more maleic acid than formula 101. Similar results can be extrapolated for the 48, 72, 96, 120, 144, 168, 192 and 216 hour time points. By the 216 hour time point (9 days), the amount of bupivacaine released from the formulations had more or less leveled off, with the total amount of drug released being the greatest for formulation 102 (approx. 76%), followed by formulation 103 (approx. 70%), followed by formulation 101 (approx. 61%), where the order is proportional to the amount of organic acid contained in the formulation. (Each formulation contained the same weight percentage of active agent). That is to say, the formulation that contained the greatest amount of organic acid had released the greatest amount of drug by the 216 hour time point. These results demonstrate the versatility of the instant amino-amide anesthetic-polyorthoester-organic acid formulations, such that the rate of drug release can be readily modulated by the addition of small amounts of an organic acid.

As mentioned above, in arriving at a formulation suitable for delivering a therapeutically effective amount of a local amino-amide anesthetic for effectively managing pain over an extended period of time, a consideration in addition to achieving an optimal release profile, is the physical stability of the formulation. As described in Example 9, in initially preparing polyorthoester-amino-amide local anesthetic formulations such as described herein but without an added organic acid, it was noted that the amino-amide local anesthetic, on several occasions, undesirably crystallized from the formulation upon standing at room temperature (under ambient conditions), typically within a period of from about 24 hours to about 1 week. The occurrence of such a phase change is indicative of a lack of physical stability of the composition, and thus, efforts were undertaken to minimize or prevent drug crystallization from the polyorthoester formulations. Moreover, crystallization of the drug within the polymer matrix undesirably slows down the rate of drug release. Thus, the introduction of various organic acid additives was explored in an effort to impede crystallization of the therapeutic agent and thereby improve stability of the instant formulations. See, e.g., Tables 8-13, demonstrating the effects of maleic acid, acetic acid, succinic acid and fumaric acid in impeding/preventing crystal formation of the illustrative anesthetic, ropivacaine. Ambient conditions are considered as standard ambient conditions of temperature (25° C.) and pressure (0.987 atm).

As shown in Table 8, a first formulation was prepared containing 5.0 weight percent ropivacaine, an aprotic solvent, and polyorthoester. The ropivacaine, which was initially dissolved in the homogeneous composition, crystallized upon cooling of the formulation to ambient temperature, despite containing a significant amount of solvent (Formulation 061, Table 8). The addition of a small amount of maleic acid, 0.6 weight percent (approx. 28 mole percent relative to ropivacaine), to a formulation containing the same amount of ropivacaine and much less solvent, was effective to provide a homogenous formulation that did not form crystals over time.

The effect of additional organic acids (acetic acid, succinic acid, fumaric acid) in enhancing and maintaining the solubilization of ropivacaine in illustrative solvents was explored. See Tables 9-11. Acetic acid is an exemplary organic mono-carboxylic acid, while succinic acid is a C4 di-carboxylic acid (butanedioic acid), and fumaric acid is an exemplary C4 di-carboxylic acid containing a central double bond. Fumaric acid is the trans isomer of butenedioic acid while maleic acid is the cis geometric isomer. The samples were prepared by first dissolving ropivacaine base in a suitable solvent such as N-methylpyrrolidone at approximately 80° C. The solutions were then allowed to stand under ambient conditions for a period ranging from about one day to one week, followed by visual inspection of the sample vials for crystal formation.

First, in turning to Table 9, it can be seen that the addition of acetic acid in amounts ranging from approximately 9 mole percent to 465 mole percent relative to ropivacaine (4.65 molar excess), was ineffective at preventing crystallization of ropivacaine from solution. Similar results were observed for solutions to which succinic acid or fumaric acid was added. In contrast, solutions to which maleic acid had been added, see Tables 12 and 13, were resistant to crystallization of drug. As shown in Table 12, solutions containing from about 16.5 mol percent maleic acid to about 60 mole percent maleic acid relative to ropivacaine exhibited either minimal crystal formation or remained in solution. Table 13 provides similar results for solutions of bupivacaine. At very small added quantities of maleic acid, e.g., at 2.5 mol % and 5 mol % maleic acid relative to bupivacaine, crystal formation was observed. See vial #s 9 and 3, respectively. However, addition to the solution of approximately 7 mol % or greater maleic acid (vial no. 7) relative to bupivacaine was effective in preventing crystallization of bupivacaine. These results indicate that in addition to its ability to notably increase the rate of release of an amino-containing drug such a caine-type drug from a polyorthoester delivery vehicle, maleic acid is also unexpectedly effective in preventing crystallization of a caine-type drug in formulations such as described herein. Thus, while the addition of other organic acids is effective to enhance the release rate of an amino-containing drug from a polyorthoester formulation as provided herein, the incorporation of a suitable amount of maleic acid is also surprisingly effective in enhancing the physical stability of the instant formulations by preventing the crystallization of the amino-containing active agent.

Liquid Excipients

The semi-solid compositions provided herein may also contain one or more excipients. Preferably, the excipient is a pharmaceutically-acceptable polyorthoester compatible liquid excipient. Such excipients are liquid at room temperature and are readily miscible with polyorthoesters. Exemplary polyorthoester compatible liquid excipients include both protic and aprotic solvents, although aprotic solvents are particularly suitable for use. Protic liquid excipients include polyethylene glycol having a molecular weight between about 200 Da and 4,000 Da, or a polyethylene glycol derivative or co-polymer having a molecular weight between about 200 Da and 4,000 Da, e.g., an end-capped PEG such as monomethoxypolyethylene glycol, or a mono-, di- or triglyceride of a C2-19 aliphatic carboxylic acid or a mixture of such acids, and alkoxylated tetrahydrofurfuryl alcohols. Additional suitable liquid excipients include C1-C4 alkyl ethers of alkoxylated tetrahydrofurfuryl alcohols, and C2-19 aliphatic carboxylic acid esters, or the like. An illustrative excipient for semi-solid formulations is monomethoxy-PEG (mPEG), having a molecular weight selected from 400, 450, 500, 550, 600 and 650.

Additional liquid excipients include aprotic solvents. Aprotic solvents suitable for use, as well as exemplary polyorthoester formulations comprising an aprotic solvent, are described in U.S. Publication No. 2014-0275046. Examples of hydrophilic biocompatible, aprotic organic solvents include, for example, amides such as N-methyl-2-pyrrolidone (NMP), 2-pyrrolidone, N-ethyl-2-pyrrolidone, N-cycylohexyl-2-pyrrolidone, dimethyl acetamide, and dimethyl formamide; esters of monobasic acids such as methyl lactate, ethyl lactate, and methyl acetate; sulfoxides such as dimethyl sulfoxide and decylmethylsulfoxide; lactones such as e-caprolactone and butyrolactone; ketones such as acetone and methyl ethyl ketone; and ethers such as dimethyl isosorbide and tetrahydrofuran.

One illustrative semi-solid composition contains a polyorthoester as described above, e.g., represented by any one of Formulas I-IV, or by Formula III, an aprotic solvent, at least one amino-containing active agent such as an amino-amide local anesthetic, and an organic acid such as described herein. In one or more embodiments, the organic acid is maleic acid. The relative concentrations of the components of the semi-solid composition will vary depending upon the amount of the basic active agent(s), polyorthoester, and polyorthoester-compatible liquid, if present. The weight percent of the polyorthoester compatible liquid can range from about 10-50 weight percent, or from about 10-40 weight percent, or from 10-30 weight percent, or from 10-25 weight percent. Exemplary amounts are about 10, 12, 15, 20, 25, 30, 35, 40, 45 or 50 weight percent of the polyorthoester-compatible liquid.

Another illustrative semi-solid composition contains a polyorthoester as described above, e.g., represented by any one of Formulas I-IV, or by Formula III, polyethylene glycol monomethylether 550 (also referred to as mPEG or monomethoxy PEG), at least one amino-containing active agent such as an amino-amide local anesthetic, and an organic acid. The relative concentrations of the components of the semi-solid composition will vary depending upon the amount of the basic active agent(s), polyorthoester, and polyorthoester-compatible liquid, if present. The weight percent of the polyorthoester compatible liquid can range from about 10-50 weight percent, or from about 10-40 weight percent, or from 10-30 weight percent, or from 10-25 weight percent. Exemplary amounts are about 10, 12, 15, 20, 25, 30, 35, 40, 45 or 50 weight percent of the polyorthoester-compatible liquid.

Active Agents

Pharmaceutical agents for use in the instant formulations are any drug that comprises a basic, i.e., amino, group. A preferred active agent is a local anesthetic of the amide- or anilide-type such as the caine class of local amide- or anilide type anesthetics. Local anesthetics belonging to this class include bupivacaine, levobupivacaine, dibucaine, mepivacaine, procaine, lidocaine, tetracaine, ropivacaine, and the like). Additional amine-based drugs include, e.g., codeine, methadone, sertraline, repaglinide, tamsulosin, sibutramine, cinacelcet, rivastigmine, lariam, ethambutol, lopinavir, chlorpheniramine, ephedrine, phenylephrine, amitriptyline, imipramine, lofepramine, clomipramine, nortriptyline, despramine, amoxapine, phenylpropanolamine, among others. One skilled in the art could readily determine additional amine-containing drugs for use in the formulations provided herein In one embodiment, the formulation comprises as the active agent ropivacaine. In another embodiment, the formulation comprises as the active agent, bupivacaine. In yet one or more additional embodiments, the formulation comprises any one or more of the caine-type local anesthetics described above. The composition of the present application may also comprise other locally acting basic active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agent" further includes biocides such as fungicides, pesticides and herbicides, plant growth promoters or inhibitors, preservatives, disinfectants, air purifiers and nutrients.

The formulation may comprise in addition to the basic active agent, one or more additional bioactive agents, which may or may not be basic (i.e., containing one or more amino groups) in nature.

The active agent or agents are dissolved or dispersed into the composition as provided herein. The concentration of the active agent in the composition may vary from about 1 wt % to 30 wt %, 1 wt % to 10 wt %, 10 wt % to 20 wt %, 2 wt % to 5 wt %, 10 wt % to 15%, or 15 wt % to 20 wt %. Representative amounts of the active agent are as follows: 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, 5 wt %, 5 wt %, 5.1 wt %, 5.2 wt %, 5.3 wt %, 5.4 wt %, 5.5 wt %, 5.6 wt %, 5.7 wt %, 5.8 wt %, 5.9 wt %, 6 wt %, 6.1 wt %, 6.2 wt %, 6.3 wt %, 6.4 wt %, 6.5 wt %, 6.6 wt %, 6.7 wt %, 6.8 wt %, 6.9 wt %, 7 wt %, 7.1 wt %, 7.2 wt %, 7.3 wt %, 7.4 wt %, 7.5 wt %, 7.6 wt %, 7.7 wt %, 7.8 wt %, 7.9 wt %, 8 wt %, 8.1 wt %, 8.2 wt %, 8.3 wt %, 8.4 wt %, 8.5 wt %, 8.6 wt %, 8.7 wt %, 8.8 wt %, 8.9 wt %, 9 wt %, 9.1 wt %, 9.2 wt %, 9.3 wt %, 9.4 wt %, 9.5 wt %, 9.6 wt %, 9.7 wt %, 9.8 wt %, 9.9 wt %, 10 wt %, 11 wt %, 11.1 wt %, 11.2 wt %, 11.3 wt %, 11.4 wt %, 11.5 wt %, 11.6 wt %, 11.7 wt %, 11.8 wt %, 11.9 wt %, 12 wt %, 12.1 wt %, 12.2 wt %, 12.3 wt %, 12.4 wt %, 12.5 wt %, 12.6 wt %, 12.7 wt %, 12.8 wt %, 12.9 wt %, 13 wt %, 13.1 wt %, 13.2 wt %, 13.3 wt %, 13.4 wt %, 13.5 wt %, 13.6 wt %, 13.7 wt %, 13.8 wt %, 13.9 wt %, 14 wt %, 14.1 wt %, 14.2 wt %, 14.3 wt %, 14.4 wt %, 14.5 wt %, 14.6 wt %, 14.7 wt %, 14.8 wt %, 14.9 wt %, 15 wt %, 15 wt %, 15.1 wt %, 15.2 wt %, 15.3 wt %, 15.4 wt %, 5.5 wt %, 15.6 wt %, 15.7 wt %, 15.8 wt %, 15.9 wt %, 16 wt %, 16.1 wt %, 16.2 wt %, 16.3 wt %, 16.4 wt %, 16.5 wt %, 16.6 wt %, 16.7 wt %, 16.8 wt %, 16.9 wt %, 17 wt %, 17.1 wt %, 17.2 wt %, 17.3 wt %, 17.4 wt %, 17.5 wt %, 17.6 wt %, 17.7 wt %, 17.8 wt %, 17.9 wt %, 18 wt %, 18.1 wt %, 18.2 wt %, 18.3 wt %, 18.4 wt %, 18.5 wt %, 18.6 wt %, 18.7 wt %, 18.8 wt %, 18.9 wt %, 19 wt %, 19.1 wt %, 19.2 wt %, 19.3 wt %, 19.4 wt %, 19.5 wt %, 19.6 wt %, 19.7 wt %, 19.8 wt %, 19.9 wt %, 20 wt %, 21 wt %, 22 wt %, 23 wt %, 24 wt %, 25 wt %, 26 wt %, 27 wt %. 28 wt %, 29 wt % and 30 wt %.

Method of Preparation

The composition, typically a semi-solid composition, sometimes referred to as a delivery vehicle, is typically prepared by mixing or blending the polyorthoester, the organic acid, and an optional polyorthoester-compatible liquid. The mixing or blending can be performed by any suitable method, and by addition of formulation components in any order, generally but not necessarily at a temperature less than about 80° C., or less than about 50° C., e.g., at room temperature, although in certain instances, depending upon the nature of the materials, mixing or blending may be carried out at higher temperatures, e.g., from about 25 to 100° C., or from about 35 to 85° C. The mixing or blending is generally carried out in the absence of additional solvents, to obtain a homogeneous, flowable and non-tacky formulation at room temperature.

For example, the organic acid is first dissolved in the polyorthoester-compatible liquid, e.g., an aprotic solvent, to which is added a desired amount of the amino-amide drug (e.g., ropivacaine, bupivacaine, or the like). The resulting solution is then stirred, and optionally heated (e.g., to from 30° C. to about 100° C.), depending on the boiling point of the organic acid and drug stability, to thereby dissolve the amino-amide drug, followed by addition of the polyorthoester and any other formulations components. The drug-polyorthoester-organic acid composition is then mixed, optionally at an elevated temperature, until homogeneous. The instant formulations may be non-homogenous, i.e., contain suspensions of drug or other components, although homogenous formulations are generally preferred.

The polyorthoester-compatible liquid, e.g., aprotic solvent, is typically added to the compositions in an amount ranging from about 10 percent to about 70 percent by weight, relative to the total weight of the composition. The liquid may be present in the composition in an amount ranging from about 20 percent to about 50 percent by weight. In other embodiments, the liquid is present in the composition in an amount ranging from about 10-60 wt %, 15-60 wt %, 15-50 wt %, 20-60 wt %, 25-50 wt %, 30-70 wt %, 30-60 wt %, 30-50 wt %, 35-70 wt %, 35-60 wt % or 35-50 wt %.

The amount of the polyorthoester in the composition generally ranges from about 1% to about 99% by weight. Illustrative amounts of polyorthoester in the composition are from about 5% to about 90% by weight, or from about 10% to about 90% by weight, or from about 20% to about 90% by weight, or from about 30% to about 85% by weight, or from about 40% to about 85% by weight.

The concentration of the amino-containing active agent in the composition may vary from about 1 wt % to 30 wt %, or from about 1 wt % to 10 wt %, or from about 10 wt % to 20 wt %, or from about 2 wt % to 5 wt %, or from about 10 wt % to 15%, or from about 15 wt % to 20 wt %.

As described above, generally, the formulation comprises from about 1 mole percent to about 95 mole percent of an organic acid relative to the amino-containing therapeutic agent such as an amino-amide local anesthetic. More typically, the composition comprises 10-80 mole percent of a mono-carboxylic acid, or from about 10-40 mole percent of a di-carboxylic acid, or from about 10 to 25 mole percent of a tri-carboxylic acid. Typically, the organic acid is present in less than an equimolar amount when compared to the amino-amide anesthetic, such that the therapeutic agent is present as a mixed salt-base. Generally, due to the low molecular weight of the organic acid excipient, the composition comprises a small quantity by weight of the organic acid. Illustrative weight percentages of the organic acid are from about 0.01 wt % to about 5 wt %, or from about 0.01 wt % to about 3 wt %, or from about 01. wt % to about 2 wt %, or from about 0.1 wt % to about 1 wt %. Illustrative weight percentages of the organic acid are 0.01 wt %, 0.02 wt %, 0.03 wt %, 0.04 wt %, 0.05 wt %, 0.06 wt %, 0.07 wt %, 0.08 wt %, 0.09 wt %, 0.10 wt %, 0.15 wt %, 0.20 wt %, 0.25 wt %, 0.30 wt %, 0.35 wt %, 0.40 wt %, 0.45 wt %, 0.50 wt %, 0.55 wt %, 0.60 wt %, 0.65 wt %, 0.70 wt %, 0.75 wt %, 0.80 wt %, 0.85 wt %, 0.90 wt %, 0.95 wt %, 1 wt %, 1.5 wt %, 2.0 wt %, 2.5 wt %, 3 wt %, 3.5 wt %, 4 wt %, 4.5 wt %, 5.0 wt %, including all ranges between any two of the foregoing weight percentages. The amount of the organic acid additive comprised in the formulation will depend, at least in part, upon the identity of the particular active agent, the amount of active agent contained in the formulation, the particular polyorthoester, amount thereof, and desired delivery profile.

Illustrative formulations, to which the instant closure is not limited, are provided in the examples. Examples of additional formulations suitable for use include those comprising a polyorthoester, from about 1 wt % bupivacaine or ropivacaine to about 10 wt % bupivacaine or ropivacaine, and from about 0.01 wt % to about 1.5 wt % organic acid such as maleic acid. The formulation may also include a polyorthoester-compatible liquid, e.g., a protic or aprotic solvent as described herein. Particularly suitable solvents include N-methyl-2-pyrrolidone, (NMP), dimethyl acetamide, and dimethyl formamide, and dimethyl sulfoxide, or additional aprotic solvents as described herein. For example, representative polyorthoester formulations comprise 5 wt % bupivacaine and 0.6 wt % maleic acid, or 2.5 wt % bupivacaine and 0.15 wt % maleic acid, or 2.5 wt % bupivacaine and 0.05 wt % maleic acid, optionally in the presence of one or more polyorthoester-compatible liquids, excipients, or additives. For example, additional representative polyorthoester formulations comprise 5 wt % ropivacaine and 0.6 wt % maleic acid, or 2.5 wt % ropivacaine and 0.15 wt % maleic acid, or 2.5 wt % ropivacaine and 0.05 wt % maleic acid, optionally in the presence of one or more polyorthoester-compatible liquids, excipients, or additives.

Although any polyester may be used, one particularly suitable polyorthoester is represented by the structure shown as Formula III,

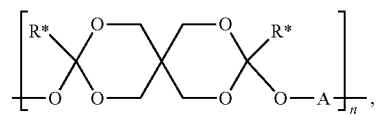

where R* is a methyl, ethyl, propyl or butyl, n is the number of repeating units and is an integer ranging from 5 to 400, and A in each subunit is $R^1$ or $R^3$. In some cases, R* is ethyl and A corresponds to $R^1$, where $R^1$ is

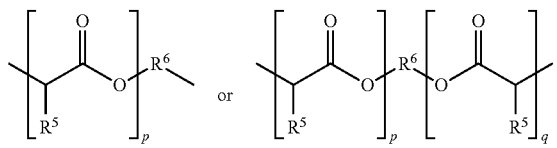

where p and q are each independently integers ranging from about 1 to 20, each $R^5$ is independently hydrogen or $C_{1-4}$ alkyl; and $R^6$ is:

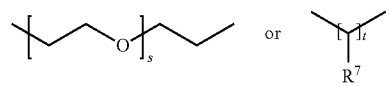

where s is an integer from 0 to 10; t is an integer from 2 to 30; and $R^7$ is hydrogen or $C_{1-4}$ alkyl, e.g., is C1, C2, C3, or C4 alkyl. In some embodiments, $R^7$ is H. $R^3$ is, e.g.,

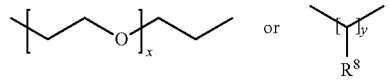

and x is an integer ranging from 1 to 100, or, is selected from 0, 1, 2, 3, 4, and 5; y is an integer in a range from 2 to 30; and $R^8$ is hydrogen or $C_{1-4}$ alkyl. In some instances, $R^8$ is a C1, C2, C3 or C4 alkyl. In yet other instances, $R^8$ is H.

For example, in some particular formulations, the polyorthoester is described by Formula III, where A is $R^1$ or $R^3$, where $R^1$ is

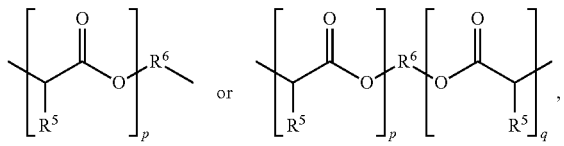

where p and q are each independently selected from 1, 2, 3, 4, 5, 6, 7, 8, 9, 10, 11, 12, 13, 14, 15, 16, 17, 18, 19, and 20 in any repeating unit, where the average number of p or the average number of the sum of p and q (p+q) is between about 1 and 7; x and s are each independently an integer ranging from 0 to 10; and t and y are each independently an integer ranging from 2 to 30. In some formulations of the polyorthoester of Formula III, the sum of p and q is 1, 2, 3, 4, 5, 6 or 7 in any repeating unit of $R^1$ and $R^5$ is, e.g., H.

The polyorthoester of Formula III may also be one in which, for example, A is $R^1$ or $R_3$, where $R^1$ is

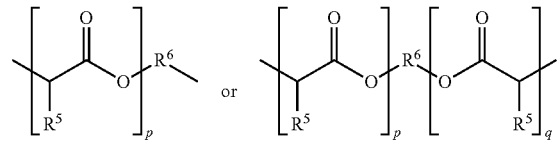

and p and q are each independently integers ranging from about 1 and 20, about 1 and 15, or about 1 and 10 in any repeating unit of $R^1$, where the average number of p or the average number of the sum of p and q (i.e., p+q) is between about 1 and 7. For example, in reference to the structures above, in some instances, x and s each independently range from 0 to about 7 or from 1 to about 5, and e.g., t and y each independently range from 2 to 10.

In certain polyorthoesters defined by the structures above, R5 is hydrogen or methyl.

In other particular examples, s and x are each independently selected from 1, 2, 3, 4, 5, 6, 7 and 8. In some instances, s is 2 and/or x is 2.

In some embodiments, the polyorthoester comprises alternating residues of 3,9-diethyl-3,9-2,4,8,10-tetraoxaspiro[5.5]undecane-3,9-diyl and A:

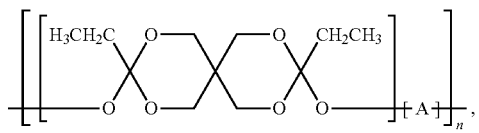

where A is as described above.

The rate of release of the active agent (e.g., drug) can be controlled by adjusting the composition and amount of the polyorthoester polymer and/or by the selection and quantity of the organic acid that is used in combination with the basic drug. The composition of the polyorthoester polymer (i.e., the type of monomer used or the ratio of monomers for copolymers or terpolymers, the end groups on the polymer chains, and the molecular weight of the polymer) will determine the hydrophilicity or lipophilicity of the polymer material as well as contribute to the degradation time of the polymer depot. More hydrophilic polymers (e.g., polyorthoesters wherein the diol monomer is hydrophilic, e.g., triethylene glycol, tetraethylene glycol, or polyethylene glycol and the like) are used in applications where faster release rates and shorter durations of release are needed. The composition includes the active agent in an amount effective to provide the desired therapeutic effect over the release period. The incorporation of the organic acid is effective, in the case of basic drugs, to accelerate the release rate of drug from the composition at the early stages of drug delivery, e.g., from administration to about day 2 or 3. After about day 3, the rate of release of the basic bioactive agent remaining in the composition is typically driven by diffusion or dissolution from the composition as it biodegrades in the body.

While the singular form is used to describe the polyorthoester and the organic acid in this application, it is understood that more than one polyorthoester and/or more than one organic acid selected from the groups described above may be used in the delivery system. In some embodiments of the herein described methods and compositions, the compositions further comprise one or more additional excipients. Preferred excipients are those that do not influence the release of the basic active agent from the composition.

It is also understood that while not required, other pharmaceutically acceptable inert agents such as coloring agents and preservatives may also be incorporated into the composition.

Method of Treatment

The compositions provided can be used, for example, in managing acute or chronic pain in a patient. Accordingly, methods of ameliorating pain, managing pain, treating pain and/or providing local anesthesia to a patient in need thereof are provided. Also provided is a method for the prophylactic treatment of pain, such as in the situation of managing or treating post-operative pain.

Also provided is a method for enhancing/increasing the release rate of a basic, i.e., amino-containing, drug comprised in a polyorthoester formulation by incorporating into the formulation an organic acid. The addition of the organic acid is effective to increase the rate of release of the basic (i.e., alkaline) drug from the polyorthoester formulation over that observed in the absence of the organic acid. More particularly, in one or more embodiments, incorporation of the organic acid is effective to increase the rate of release of the amino-containing drug from the polyorthoester formulation in comparison to a formulation comprising the same components in the same relative amounts but absent the organic acid, when measured either in an in-vitro test at 37° C. during the first 24 hours after initiation of the test.

Preferably, the incorporation of the organic acid is effective to promote release of a significant portion of the alkaline active agent from the composition, such that 75 weight percent or more, or 80% by weight or more of the drug is released from the composition, either in vitro or in vivo, over a period of up to about 5 days, or up to about 3 days, following administration or initiation of an in vitro drug release experiment (e.g., as described in Example 2), or for a period of about 1 day to about 3 days, or from about 1 day to 5 days, or from about 1 day to 4 days, or from about 2 days to 5 days, or from about 2 days to 4 days, or from about 2 days to 3 days, or from about 3 days to 5 days. Typically, in the absence of the organic acid, the release of the alkaline drug extends over a period of greater than 5 days, such that the period of time required to release at least 75% by weight, or at least 80% by weight or more of the drug is greater, and often significantly greater, than 5 days.

Also provided, in another aspect, is a method of treatment. The method comprises dispensing from a needle, a composition comprising an amino-containing, alkaline drug, a polyorthoester, and an organic acid, to thereby achieve a controlled release of the alkaline drug from the composition, wherein 75 weight percent or more, or even 80% by weight or more of the drug is released from the composition over a period of about 3 days, about 4 days, or about 5 days, for example, over a period of from 3 to 5 days, e.g. for up to about 5 days, or up to about 3 days, or for a period of about 1 day to about 3 days, or from about 1 day to 5 days, or from about 1 day to 4 days, or from about 2 days to 5 days, or from about 2 days to 4 days, or from about 2 days to 3 days, or from about 3 days to 5 days.

The compositions provided herein are for use in a method of providing local anesthesia to a patient in need thereof. The treatment includes administering to a patient a composition as set forth herein, e.g., comprising an amide or anilide-type local anesthetic, a polyorthoester and an organic acid, to provide a rate of release of anesthetic effective for reducing or preventing pain. Local administration can be, e.g., at a nerve, into the epidural space, intrathecal, or directly to a surgical site or wound. Preferably, 75% or even 80% by weight or more of the drug is released over a period of up to about 5 days.

A method for providing pain relief to a patient in need thereof is provided, where the method comprises providing a composition as described herein, and instructing that the composition be administered to the patient to provide pain relief for an extended period. In one embodiment, the extended period is for at least about 5 days. In another embodiment, the extended period is for up to about 5 days. In still another embodiment, the extended period is from about 1 day to at least about 5 days or from about 1 day to up to about 5 days. In yet another embodiment, the extended period is for about 3 days. In still another embodiment, the extended period is from about 1 day to at least about 3 days, or from about 1 day to up to about 3 days, or is up to about from 3 days to 5 days.

The compositions and delivery systems provided herein may also be used for managing, reducing or treating acute or chronic pain. The compositions may also be used for the prophylactic treatment of acute or chronic pain. Acute pain can be associated with, for example, surgery, broken bones, dental work, burns or cuts or labor and childbirth. Chronic pain can be associated with, for example, headache, low back pain, cancer pain, arthritis pain, neurogenic pain and psychogenic pain.

In terms of administration for any of the methods described herein, the compositions may be injected, instilled, or applied with standard syringes and needles (e.g., about 16 gauge), or may be applied with, e.g., a spray applicator. The compositions may be injected subcutaneously, intradermally or intramuscularly. The compositions may be applied to a wound topically or subcutaneously. The compositions may also be applied perineurally. The compositions may be applied using various methods known in the art, including by syringe, injectable or tube dispenser.

In one aspect, the compositions described herein which comprise an amino-amide local anesthetic and an organic acid are contemplated for administration as a peripheral nerve block. In particular, the compositions described above are contemplated for use as a nerve block. A peripheral nerve block involves the introduction of an active agent near or in a peripheral nerve for the reduction of pain or to provide numbness. Types of peripheral nerve blocks include but are not limited to motor, sensory, differential, and autonomic blocks, and additionally, include but are not limited to brachial plexus (axillary, interscalene, supraclavicular, infraclavicular), individual upper extremity nerve blocks (median, radial, ulnar, musculocutaneous, axillary), sciatic, ankle, metatarsal, oral, femoral, popliteal fossa, saphenous, distal, digital, deep peroneal, superficial peroneal, tibial, sural, and saphenous blocks.

Features of the Composition

The release rates of a local anesthetic from formulations comprising the exemplary active agent, ropivacaine, and varying amounts of an organic acid excipient were examined. The results are shown in FIG. 1. The formulations each comprised 5 weight percent ropivacaine free base, and 20 weight percent polyorthoester. Each formulation contained different amounts of an organic acid excipient: 0 wt %, 10 wt %, 20 wt %, 30 wt %, and 40 wt % organic acid excipient. The organic acid employed was a C4 di-acid. The composition absent the organic acid excipient released the drug at a slow rate, such that at 48 hours, only about 15 wt % drug had been released. At 96 hours, only 30 wt % drug had been released from the composition lacking an organic acid excipient. In contrast, the formulations containing from 10 wt % to 40 wt % of the organic acid excipient each exhibited a markedly improved rate of release ropivacaine. The rate of release of drug for the organic acid-containing formulations was greatly accelerated in comparison to the control formulation without the organic acid, as evidenced by the steep slopes of the graphs from 0-24 hours, or from 0-48 hours, and even from 0-72 hours. For example, at 72 hours, the organic acid-containing formulations had released from about 80 wt % to 50 wt % drug (from highest to lowest concentration of organic acid excipient), while the control formulation had released only about 25 wt % drug at the same time point. The composition comprising the greatest amount of organic acid generally exhibited the highest release rate of drug over days 1-3. Compositions comprising a greater weight percent of organic acid excipient generally exhibited a faster rate of release of drug for each of the time points measured (as can be seen by a comparison of the slope of each of the plots), and thus had released a greater quantity of drug for each of the time points measured. The graphs illustrate the ability of the added organic carboxylic acid to significantly increase the amount of basic drug, i.e., ropivacaine, released from the formulation, particularly over the first two or 3 days following administration. The compositions exhibit a rate of drug release for the first 2 or 3 days following administration that is greater than the rate of drug release over days 4-5 and beyond. Thus, upon incorporation of an organic acid, formulations are provided that can provide a high local concentration of an anesthetic or other amine-containing drug for 2-3 days post administration, followed by a diminished release of drug over days 3-5. The organic acid is effective to promote an initial enhanced rate of hydrolysis of the polyorthoester to thereby provide initial rapid release of drug, followed by a slower, conventional hydrolysis of the polyorthoester matrix over days 3-5 and beyond.

Pharmacokinetic data for ropivacaine formulations as described above, both absent an organic acid excipient, and containing 0.2 wt % to 0.6 wt % of an organic acid, were consistent with the release rate data described above and shown in FIG. 1. The pharmacokinetic results are shown in FIG. 2, where concentration of ropivacaine in ng/mL is provided on the x-axis, versus time, in hours, on the y-axis. The pharmacokinetic data is consistent with the in vitro data and illustrates increased concentrations of the active agent, ropivacaine, up to about 120 hours for the organic acid-comprising formulation when compared to the formulation absent the organic acid excipient, consistent with increased release of drug from the organic-acid excipient comprising-formulation. Indeed, the formulation comprising the organic acid excipient was effective to provide ropivacaine levels from about 900 ng/mL at the initial time measurement (essentially time zero) to about 250 ng/mL at 72 hours, while the formulation absent the organic acid excipient was effective to provide ropivacaine levels of about 400 ng/mL at the initial time point (time zero) to about 50 ng/mL at 72 hours. The incorporation of the organic acid excipient was effective to notably improve the release rate of the exemplary drug, ropivacaine, from the polyorthoester formulation, especially at the initial stages of delivery, such that the ropivacaine levels were notably higher through day 5.

EXAMPLES

The following examples are illustrative in nature and are in no way intended to be limiting.

Materials: Each of the illustrative formulations described in Examples 1-8 comprises a polyorthoester of formula III, comprising 80% triethylene glycol (TEG) and 20% TEG-glycolide (comprising on average 2 glycolides per subunit, i.e., TEG-diglycolide). See, e.g., U.S. Pat. No. 8,252,305, Example 1(d).

Example 1

5% Ropivacaine Polyorthoester Formulations Comprising Various Amounts of an Exemplary Organic Di-Carboxylic Acid Viscous, semi-solid formulations suitable for instillation into an incision were prepared as follows. The formulations comprised 20% by weight of a representative polyorthoester, 5 weight percent ropivacaine free base (i.e., ropivacaine was used in its free base form to prepare the formulations), and varying amounts of a representative organic di-carboxylic acid, maleic acid: 0 wt or mol %, 10 mol %, 20 mol %, 30 mol %, and 40 mol %. The molar percentages of maleic acid are relative to moles ropivacaine in the formulation. For example, Formulation 001 contains approximately 16.4 mmols of ropivacaine and approximately 1.72 mmols of maleic acid, or 10 mol percent maleic acid relative to the ropivacaine. The compositions of ropivacaine with an organic acid (maleic acid) were prepared by initially dissolving the organic acid in an aprotic solvent. As illustrated in the table below, N-methyl pyrrolidone was used as the aprotic solvent, although any aprotic solvent (or protic solvent) may be used. An appropriate amount of ropivacaine was then added and dissolved with the organic acid solution at approximately 80° C. The drug solution was then mixed with the appropriate amount of polymer (POO) at an elevated temperature, until homogenous. Exemplary compositions are presented in Table 1 below.

TABLE 1

Ropivacaine/Polyorthoester/Aprotic Solvent/Organic Acid Formulations, Weight Percentages

| Formulation ID | Solvent ID | Ropivacaine Base wt % | Maleic acid wt % | Wt % POE | Wt % Solvent |
|---|---|---|---|---|---|
| 000 | NMP | 5.0%* | 0% | 72.0% | 24.0% |
| 001 | NMP | 4.5% | 0.2% (10 mol %) | 74.8% | 20.5% |
| 002 | NMP | 4.5% | 0.4% (20 mol %) | 74.6% | 20.5% |
| 003 | NMP | 4.5% | 0.6% (30 mol %) | 74.4% | 20.5% |
| 004 | NMP | 4.5% | 0.8% (40 mol %) | 74.2% | 20.5% |
| 005 | NMP | 5.0% | 0.6% (30 mol %) | 75.5% | 18.9% |
| 006 | NMP | 5.0% | 0.3% (15 mo %) | 71.0% | 23.7% |
| 007 | NMP | 5.0% | 0.2% (10 mol %) | 71.1% | 23.7% |

*contained 0.25% hydrochloride salt
NMP = N-methyl pyrrolidone
POE = polyorthoester

Example 2

In-Vitro Release of Ropivacaine Compositions

The release of ropivacaine from the compositions described in Example 1 was determined by placing a small amount of the polymer formulation (approximately 50 mg) into 150 mL of phosphate buffered saline. The samples were then incubated at 37° C. with agitation. At 24 hour intervals, 1 mL samples were taken from the vials without agitation of the depot. Each sample was analyzed by HPLC to determine the concentration of ropivacaine. The cumulative drug release from the 50 mg depot was then calculated. The results are presented in Table 2. Release profiles of the active agent are shown in FIG. 1.

The graphs illustrate the ability of the added organic carboxylic acid to significantly increase the amount of basic drug, i.e., ropivacaine, released from the formulation, i.e, to transform the formulation into a rapid release formulation. Compositions comprising a greater weight percent of organic acid excipient generally exhibited a faster rate of release of drug for each of the time points measured (as can be seen by a comparison of the slope of each of the plots), and thus had released a greater quantity of drug for each of the time points measured. The compositions exhibit a rate of drug release for the first 2 or 3 days following administration that is greater than the rate of drug release over days 4-5 and beyond. Thus, addition of an organic acid, optimally at a molar percentage relative to the amino-containing drug, i.e., a 'caine' type drug, of less than 100 mol %, e.g., from about 1 mole percent to about 95 mole percent, to polyorthoester formulations such as provided herein, is effective to enhance the release of drug from the formulation to thereby provide a formulation that is effective to release at least approximately 75% of drug from the formulation in 5 days or fewer, e.g., in from 1-5 days, when evaluated by an in-vitro test method as described in this example. As shown in FIG. 1, at approximately 48 hours, only about 16% ropivaine had been released from the composition that did not contain organic acid, while in contrast, at the same 48 hour time point, compositions containing 10 mol %, 20 mol %, 30 mol % and 40 mol % organic acid had released approximately 38%, 52%, 59% and 73% ropivacaine, respectively. As can be seen, the initial release of drug was notably improved by addition of even small amounts of organic acid, e.g., from 10 mol % to 40 mol % of the di-acid, maleic acid. That is to say, a non-rapid release polyorthoester formulation was converted to a rapid release formulation by the addition of even small amounts of an organic acid such as maleic acid.

TABLE 2A

In Vitro Release of Ropivacaine

Percent Ropivacaine Released for Compositions

| Composition # | 24 hrs | 48 hrs | 72 hrs | 96 hrs | 120 hrs | 144 hrs | 168 hrs | 192 hrs |
|---|---|---|---|---|---|---|---|---|
| 000 | 8.30  | 16.36 | 23.52 | 30.05 | N/S   | N/S   | 45.49 | N/S   |
| 001 | 16.79 | 37.74 | 50.02 | 60.81 | 69.26 | N/S   | N/S   | N/S   |
| 002 | 28.06 | 51.68 | 63.71 | 73.79 | 77.21 | N/S   | N/S   | N/S   |
| 003 | 38.21 | 59.00 | 69.24 | 74.88 | 79.81 | N/S   | N/S   | N/S   |
| 004 | 52.43 | 72.62 | 78.78 | 83.37 | 87.91 | N/S   | N/S   | N/S   |
| 005 | 26.26 | 52.08 | 63.75 | 73.89 | 83.20 | 88.67 | 90.37 | 90.66 |
| 006 | 12.06 | 34.80 | 50.08 | 62.45 | 72.96 | 82.35 | 87.99 | 91.39 |
| 007 | 11.74 | 30.77 | 43.13 | 53.10 | 64.93 | 74.81 | 80.88 | 84.54 |

N/S—not sampled

Example 3

Pharmacokinetics of a 5% Ropivacaine Polyorthoester Formulation Comprising an Exemplary Organic Di-Carboxylic Acid Excipient in Canines The pharmacokinetics of an exemplary polyorthoester-ropivacaine formulation both with and without added organic acid excipient was determined. In a series of pharmacokinetic studies, ten dogs (5 male-5 female) were treated with Formulation 000 (without organic acid) and with Formulation 005 (containing 30 mol % maleic acid relative to moles ropivacaine) as described in Example 1. Compositions of ropivacaine with an organic acid were prepared by dissolving various molar ratios of organic acid in an aprotic solvent, although a protic solvent may also be employed. The appropriate amount of ropivacaine was added and dissolved with the organic acid solution at approximately 80° C. The drug solution was then mixed with the appropriate amount of polyorthoester polymer at an elevated temperature until homogenous. Dogs received the entire contents of one syringe containing sufficient polyorthoester formulation to deliver approximately 100 mg of ropivacaine. Plasma samples were taken from each dog at the following time points: −24, 1, 6, 12, 24, 48, 72, 96, 120, 144, and 168 hours and frozen. The plasma samples were subsequently analyzed by LC/MS/MS for ropivacaine. A plot of the plasma concentration of ropivacaine versus time is presented in FIG. 2, where concentration of ropivacaine in ng/mL is provided on the x-axis, while time, in hours, is shown on the y-axis. Both formulations provided measurable plasma concentrations of ropivacaine for at least 5 days, however, the formulation containing the added maleic acid released drug faster than the formulation with the free base alone.

The pharmacokinetic data is consistent with the in vitro data and illustrates increased concentrations of the active agent, ropivacaine, detected in plasma up to about 120 hours post-administration for the organic acid-comprising formulation when compared to the formulation absent the organic acid excipient, consistent with the increased release rate of drug from the organic-acid excipient comprising-formulation as described in Example 2. The data shown in FIG. 2 is provided below in Table 2-B.

TABLE 2-B

In Vivo Release of Ropivacaine in Canine Study

Ropivacaine Concentration in Plasma, ng/mL

| Comp # | 1 hrs | 3 hrs | 6 hrs | 10 hrs | 24 hrs | 30 hrs | 48 hrs | 72 hrs | 96 hrs | 120 hrs | 144 hrs | 168 hrs |
|---|---|---|---|---|---|---|---|---|---|---|---|---|
| 005 (with added organic acid) | 675.2 | 617.4 | 433 | 302 | 278.8 | 234.6 | 249.98 | 148.64 | 61.62 | 36.2 | 16.72 | 10.5 |
| 000 | 207 | N/S | 117.6 | N/S | 133.43 | N/S | 89.37 | 41.8 | 38.3 | 27.6 | 30.7 | 24.1 |

N/S—not sampled

Additional time points for formulation 000 include 192 hours (15.03 ng/mL); 216 hours (18.63 ng/mL; and 240 hours (13.3 ng/mL). This in vivo data illustrates that the incorporation of even small amounts of an organic acid such as maleic acid, in this case, 0.6 weight percent of the polyorthoester formulation, can notably impact the release of amino-containing active agent from the formulation, particularly at the early stages post-administration. At the 1 hour time point, plasma levels of drug were 3-fold higher than for the formulation that did not contain organic acid. At 6 hours post-administration, plasma drug levels were 3.7 times higher for the organic acid-containing formulation, while at 24 hours, plasma drug levels were approximately twice as high. This trend continued with plasma drug levels 2.8 times greater for the organic acid containing formulation at 48 hours, and 3.6 times greater at 72 hours. A striking difference in the release profile of the polyorthoester formulation can thereby be attained by the addition of organic acid. This effect is particularly advantageous for drugs such as local anesthetics that are often applied locally, for example, at a wound or incision site, for the treatment of pain.

Example 4

Bupivacaine Delivery Systems Comprising an Aprotic Solvent

Compositions containing approximately 66% to 67 wt % polyorthoester of formula III, between approximately 16 wt % and 17 wt % of an aprotic solvent, N-methyl pyrrolidone, approximately 15 wt % bupivacaine base, and 1 wt % to 1.7 wt % organic acid were prepared. Weight percentages maleic acid correspond to mole percentages of approximately 16.5-29 mole percent organic acid relative to moles bupivacaine comprised within the polyorthoester formulation. The compositions were prepared by first dissolving the appropriate amount of organic acid in the appropriate amount of aprotic solvent at approximately 80° C. and then dissolving the appropriate amount of bupivacaine base. The drug solution was then mixed with the appropriate amount of polymer at an elevated temperature until homogenous. Exemplary compositions are presented in Table 3.

TABLE 3

Bupivacaine/Polyorthoester/Aprotic Solvent/Organic Acid Formulations

| Formulation ID | Solvent ID | Wt % Bupivacaine | Wt % Maleic Acid | Wt % POE | Wt % Solvent |
|---|---|---|---|---|---|
| 101 | NMP | 15.0% | 1.0% (16.5 mol %) | 67.1% | 16.9% |
| 102 | NMP | 15.0% | 1.7% (28 mol %) | 66.5% | 16.8% |
| 0103 | NMP | 15.0% | 1.6% (26.5 mo %) | 66.4% | 17.0% |
| 0104 | NMP | 5.0% | 0.4% (20 mol %) | 79.6% | 15.0% |
| 0105 | NMP | 5.0% | 0.8% (40 mol %) | 79.2% | 15.0% |

NMP = N-methyl pyrrolidone

Example 5

In-Vitro Release of Bupivacaine Compositions

The release of bupivacaine from the compositions described in Example 4 (101-103) was determined by placing a small amount of the polymer formulation (approximately 50 mg) into 150 mL of phosphate buffered saline. The samples were then incubated at 37° C. with agitation. At 24 hour intervals, 1 mL samples were taken from the vials without any agitation of the depot. Each sample was analyzed by HPLC to determine the concentration of bupivacaine. The cumulative drug release from the 50 mg depot was then calculated.

TABLE 4

In Vitro Release of Bupivacaine

| Composition # | | 24 hrs | 48 hrs | 72 hrs | 96 hrs | 120 hrs | 144 hrs | 168 hrs | 192 hrs | 216 hrs |
|---|---|---|---|---|---|---|---|---|---|---|
| 101 | A-168 | 15.74 | 28.75 | 34.90 | 39.37 | 44.65 | 48.67 | 51.92 | 57.46 | 61.42 |
| 102 | A-169 | 33.12 | 45.93 | 52.46 | 58.24 | 63.45 | 67.27 | 69.80 | 73.83 | 76.37 |
| 103 | A-170 | 26.53 | 40.24 | 45.84 | 49.94 | 54.94 | 58.53 | 61.30 | 66.40 | 70.01 |

As can be seen from the results in Table 4, the cumulative amount of bupivacaine released from the formulations at each time point was the greatest for the formulation containing the greatest amount of organic acid (Composition 102). At the 24 hour time point, over 2 times the quantity of bupivacaine had been released from formulation 102 relative to formulation 101, where formulation 102 contained about 1.7 times more maleic acid than formula 101. At the 24 hour time point, about 1.7 times the amount of bupivacaine had been released from formulation 103 relative to formulation 101, where formulation 103 contained about 1.6 times more maleic acid than formula 101. Similar results can be extrapolated for the 48, 72, 96, 120, 144, 168, 192 and 216 hour time points. By the 216 hour time point (9 days), the amount of bupivacaine released from the formulations had more or less leveled off, with the total amount of drug released being the greatest for formulation 102 (approx. 76%), followed by formulation 103 (approx. 70%), followed by formulation 101 (approx. 61%), where the order is proportional to the amount of organic acid contained in the formulation. (Each formulation contained the same weight percentage of active agent). That is to say, the formulation that contained the greatest amount of organic acid had released the greatest amount of drug by the 216 hour time point. These results demonstrate the versatility of the instant amino-amide anesthetic-polyorthoester-organic acid formulations, such that the rate of drug release can be readily modulated by the addition of small amounts of an organic acid. The addition of a suitable amount of organic acid is effective to transform a slow-release formulation into a rapid release formulation as demonstrated herein.

Example 6

Ropivacaine Delivery Systems Comprising an Aprotic Solvent

Compositions containing between 45 wt % to 80 wt % polyorthoester of formula III, between 20 wt % and 45 wt % of an aprotic solvent, and between 4 wt % and 22.0 wt % ropivacaine were prepared. Ropivacaine used in these compositions optionally contained a combination of ropivacaine base and ropivacaine hydrochloride. For compositions where the ropivacaine was in solution, the composition was prepared by first the dissolving the appropriate amount of ropivacaine base into the appropriate amount of aprotic solvent at approximately 80° C. The drug solution was then mixed with the appropriate amount of polymer at an elevated temperature, until homogenous. For compositions where the ropivacaine was in suspension, the composition was prepared by first combining the appropriate amount of polyorthoester polymer and the appropriate amount of aprotic solvent at approximately 80° C. The solution was cooled to approximately room temperature and the ropivacaine was added to the polymer solvent mixture. Exemplary compositions are presented in Table 5. To enhance the release of ropivacaine from the formulations described below, and/or to impede the formation of crystalline ropivacaine upon storage, an organic acid as described herein may be added to the formulation. Typically, the amount of organic acid added to any one or more of the formulations below will range from about 10-80 mole percent relative to ropivacaine for a mono-carboxylic acid, from about 10-40 mole percent relative to ropivacaine for a di-carboxylic acid, and from about 10-25 mole percent relative to ropivacaine for a tri-carboxylic acid, although addition of from about 1 mol percent to about 95 mole percent is contemplated.

TABLE 5

Ropivacaine Delivery Systems: Polyorthoester-Aprotic Solvent Compositions

| Formulation ID | Solvent | Ropivacaine Base % | Ropivacaine HCl Salt % | % POE | % Solvent | Ropivacaine Composition Form |
|---|---|---|---|---|---|---|
| 010 | DMAc | 22.00% | 0.00% | 53.7% | 24.2% | Suspension |
| 020 | NMP | 9.10% | 0.50% | 45.2% | 45.2% | Dissolved |
| 030 | NMP | 4.75% | 0.25% | 72.0% | 24.0% | Dissolved |
| 040 | DMAc | 20.70% | 0.00% | 56.4% | 22.9% | Suspension |
| 050 | NMP | 10.00% | 0.00% | 45.0% | 45.0% | Dissolved |
| 060 | NMP | 4.50% | 0.50% | 71.0% | 24.0% | Dissolved |
| 070 | NMP | 4.75% | 0.25% | 66.5% | 28.5% | Dissolved |
| 080 | NMP | 4.00% | 1.00% | 80.0% | 20.0% | Dissolved |
| 090 | NMP | 3.50% | 1.50% | 80.0% | 20.0% | Dissolved |
| 011 | DMSO NMP | 3.96% | 0.24% | 68.5% | 4.7% DMSO 22.5% NMP | Dissolved |
| 012 | NMP | 3.80% | .020% | 72.0% | 24.0% | Dissolved |
| 013 | DMSO | 9.00% | 0.00% | 49.7% | 41.3% | Dissolved |
| 014 | DMSO | 4.15% | 0.85% | 52.0% | 43.0% | Dissolved |
| 015 | NMP | 3.60% | 0.40% | 67.1% | 28.9% | Dissolved |
| 016 | NMP | 9.0% | 1.0% | 65.0% | 25.0% | Suspension |
| 017 | NMP | 7.5% | 2.5% | 65.0% | 25.0% | Suspension |
| 018 | NMP | 5.0% | 5.0% | 65.0% | 25.0% | Suspension |
| 019 | DMAc | 9.0% | 1.1% | 71.9% | 17.9% | Suspension |
| 020 | DMAc | 7.4% | 2.6% | 72.0% | 18.0% | Suspension |
| 021 | DMAc | 5.0% | 5.0% | 72.0% | 18.0% | Suspension |

DMAC = dimethyl acetamide
DMSO = dimethylsulfoxide

Example 7

In-Vitro Release of Ropivacaine Compositions

The release of ropivacaine from the compositions described in Example 6 was determined by placing a small amount of the polymer formulation (approximately 50 mg) into 150 mL of phosphate buffered saline. The samples were then incubated at 37° C. without agitation. At 24 hour intervals, 1 mL samples were taken from the vials without any agitation of the solution. Each sample was analyzed by HPLC to determine the concentration of ropivacaine. The cumulative drug release from the 50 mg depot was then calculated. The data is summarized in Table 6.

TABLE 6

In Vitro Release of Ropivacaine

| Composition # | Percent Ropivacaine Released for Compositions | | | | | | | | |
|---|---|---|---|---|---|---|---|---|---|
| | 24 hrs | 48 hrs | 72 hrs | 96 hrs | 120 hrs | 144 hrs | 168 hrs | 192 hrs | 216 hrs |
| 020 | 35.78 | 72.20 | 83.30 | 86.60 | 91.44 | 95.45 | N/S | N/S | N/S |
| 030 | 45.26 | 51.67 | 52.54 | 58.65 | 67.06 | 69.99 | N/S | N/S | N/S |
| 040 | 25.09 | 34.35 | 37.08 | 45.69 | 55.92 | 63.29 | N/S | N/S | N/S |
| 060 | 26.55 | 43.97 | 57.01 | 71.73 | N/S | N/S | 93.96 | 97.35 | |
| 070 | 29.28 | 50.98 | 63.79 | 79.06 | 112.86 | 121.67 | N/S | N/S | N/S |
| 011 | 8.61 | 18.02 | 25.49 | 34.17 | N/S | N/S | 59.53 | 81.58 | N/S |
| 013 | 10.03 | 29.17 | 39.27 | 58.08 | 67.97 | 77.05 | N/S | N/S | N/S |
| 014 | 20.66 | 45.77 | 48.48 | 61.73 | 76.75 | 80.08 | N/S | N/S | N/S |
| 015 | 31.80 | 40.73 | 50.54 | 54.33 | N/S | N/S | N/S | 85.13 | 89.20 |

N/S—not sampled

In considering the above compositions, the average percent ropivacaine released in vitro in 24 hours was only about 25%. To provide a rapid-release formulation comprising a polyorthoester and an amino-amide therapeutic agent, e.g., a formulation capable of providing a 3-5 day release profile, it is preferable to release about 30-40% therapeutic agent within 24 hours. To achieve this desired profile, organic acid as described herein can be incorporated into the foregoing formulations.

Example 8

Pharmacokinetic Analysis of Ropivacaine Formulations in Canines

In a series of pharmacokinetic studies, ten dogs (5 male-5 female) were treated with the formulations listed in Table 7. Dogs received the entire contents of 1 syringe containing sufficient polyorthoester formulation to deliver approximately 100 mg of ropivacaine. Plasma samples were taken from each dog at the following time points: −24, 1, 6, 12, 24, 48, 72, 96, 120, 144, and 168 hours and frozen. The plasma samples were subsequently analyzed by LC/MS/MS for ropivacaine. Although all of the formulations provided measurable plasma concentrations of ropivacaine over a period of at least 5 days, none of the formulations provided a desired rapid-release formulation effective to release at least about 75 percent or more of ropivacaine over a time period of five days.

TABLE 7

Ropivacaine Formulations Used in Pharmacokinetic Study in Canines

| Formulation ID | Solvent ID | Ropivacaine Base % | Ropivacaine HCl % | % POE | % Solvent | Ropivacaine Composition Form |
|---|---|---|---|---|---|---|
| 030 | NMP | 4.75% | 0.25% | 75.0% | 25.0% | Dissolved |
| 040 | DMAc | 20.70% | 0.00% | 56.4% | 22.9% | Suspension |

TABLE 7-continued

Ropivacaine Formulations Used in Pharmacokinetic Study in Canines

| Formulation ID | Solvent ID | Ropivacaine Base % | Ropivacaine HCl % | % POE | % Solvent | Ropivacaine Composition Form |
|---|---|---|---|---|---|---|
| 050 | NMP | 10.00% | 0.00% | 45.0% | 45.0% | Dissolved |
| 060 | NMP | 4.50% | 0.50% | 71.0% | 24.0% | Dissolved |

Example 9

Effect of Organic Acid Addition on the Stability of Ropivacaine-Polyorthoester Compositions In initially preparing polyorthoester formulations such as described herein but without an added organic acid, it was noted that the amino-amide local anesthetic, in several cases, undesirably crystallized from the formulation upon standing at room temperature (under ambient conditions), typically within a period of from about 24 hours to about 1 week. The occurrence of such a phase change is indicative of a lack of physical stability of the compositions, and thus, efforts were undertaken to minimize or prevent drug crystallization from the polyorthoester formulations. Crystallization of drug from the formulations tends to adversely impact (slow down) the rate of release of drug from the formulation, since the drug has to redissolve. Introduction of various organic acid additives was explored in an effort to impede crystallization of the therapeutic agent and thereby improve stability of the instant formulations.

A first formulation was prepared containing 5.0 weight percent ropivacaine, an aprotic solvent, and polyorthoester as described in the previous examples. The ropivacaine, which was initially dissolved in the homogeneous composition, crystallized upon cooling of the formulation to ambient temperature, despite containing a significant amount of solvent (Formulation 061, Table 8). The addition of a small amount of maleic acid, 0.6 weight percent (approx. 28 mole percent relative to ropivacaine), to a formulation containing the same amount of ropivacaine and much less solvent, was effective to provide a homogenous formulation that did not form crystals over time.

The effect of additional organic acids (acetic acid, succinic acid, fumaric acid) in enhancing and maintaining the solubilization of ropivacaine in illustrative solvents was explored. See Tables 9-11. Acetic acid is an exemplary organic mono-carboxylic acid, while succinic acid is a C4 di-carboxylic acid (butanedioic acid), and fumaric acid is an exemplary C4 di-carboxylic acid containing a central double bond. Fumaric acid is the trans isomer of butenedioic acid while maleic acid is the cis geometric isomer. The samples described below were prepared by first dissolving ropivacaine base in N-methylpyrrolidone at approximately 80° C. The solutions were then allowed to stand under ambient conditions for a period ranging from about one day to one week, followed by visual observation for the formation of crystals. Crystal formation was readily apparent by visual inspection of the sample vials. Results are described below.

First, in turning to Table 9, it can be seen that the addition of acetic acid in amounts ranging from approximately 9 mole percent to 465 mole percent relative to ropivacaine (4.65 molar excess), was ineffective at preventing crystallization of ropivacaine from solution. Similar results were observed for solutions to which succinic acid or fumaric acid was added. In contrast, solutions to which maleic acid had been added, see Tables 12 and 13, were resistant to crystallization of drug. As shown in Table 12, solutions containing from about 16.5 mol percent maleic acid to about 60 mole percent maleic acid relative to ropivacaine exhibited either minimal crystal formation or remained in solution. Table 13 provides similar results for solutions of bupivacaine. At very small added quantities of maleic acid, e.g., at 2.5 mol % and 5 mol % maleic acid relative to bupivacaine, crystal formation was observed. See vial #s 8, 9, and 3, respectively. For vial #s 8 and 3, i.e., the 5 mole percent formulations, the bupivacaine crystallized following formulation with the polyorthoester. However, addition to the solution of approximately 7 mol % or greater maleic acid (vial no. 7) relative to bupivacaine was effective to prevent crystallization of bupivacaine. These results indicate that in addition to its ability to notably increase the rate of release of an amino-containing drug such a caine-type drug from a polyorthoester formulation as described herein, maleic acid is also unexpectedly effective in preventing crystallization of a caine-type drug in formulations such as described herein. Thus, while the addition of other organic acids is effective to enhance the release rate of an amino-containing drug from a polyorthoester formulation as provided herein, the incorporation of a suitable amount of maleic acid is also surprisingly effective in enhancing the physical stability of the instant formulations by preventing the crystallization of the amino-containing active agent.

TABLE 8

Crystallization in Illustrative Polyorthoester Compositions With and Without Maleic Acid

| Formulation Lot ID | Ropivacaine wt % | NMP wt % | Maleic acid wt % | POE Wt % | Condition |
|---|---|---|---|---|---|
| 061 | 5% | 30 | 0.0 | 65.0% | Crystal |
| 005 | 5% | 18.9% | 0.6% | 75.5% | Clear |

TABLE 9

Effect of Acetic Acid on the Solubility of Ropivacaine Dissolved in N-Methylpyrrolidone

| Vial # | Wt % Ropivacaine | Wt % Solvent, NMP | % Acetic acid | Condition |
|---|---|---|---|---|
| 1 | 19.92% | 79.67% | 0.41% | crystals |
| 2 | 19.83% | 79.33% | 0.83% | crystals |
| 3 | 19.67% | 78.68% | 1.65% | crystals |
| 4 | 19.59% | 78.37% | 2.04% | crystals |
| 5 | 19 51% | 78.03% | 2.46% | crystals |
| 6 | 19.35% | 77.40% | 3.25% | crystals |
| 7 | 17.45% | 69.78% | 12.77% | crystals |
| 8 | 17.51% | 70.03% | 12.46% | crystals |
| 9 | 16.64% | 66.58% | 16.78% | crystals |

TABLE 10

Effect of Succinic Acid on the Solubility of Ropivacaine Dissolved in N-Methylpyrrolidone

| Vial # | Ropivacaine wt % | NMP wt % | Succinic acid wt % | Condition |
|---|---|---|---|---|
| 1 | 19.72% | 78.90% | 1.38% | crystals |
| 2 | 19.33% | 77.30% | 3.37% | crystals |
| 3 | 18.69% | 74.77% | 6.54% | crystals |

TABLE 11

Effect of Fumaric Acid on the Solubility of Ropivacaine Dissolved in N-Methylpyrrolidone

| Vial # | Ropivacaine wt % | NMP wt % | Fumaric acid wt % | Condition |
|---|---|---|---|---|
| 1 | 19.72% | 78.90% | 1.38% | crystals |
| 2 | 19.33% | 77.30% | 3.37% | crystals |
| 3 | 18.69% | 74.77% | 6.54% | crystals |

TABLE 12

Effect of Maleic Acid on the Solubility of Ropivacaine Dissolved in N-Methylpyrrolidone

| Vial # | Ropivacaine wt % | NMP wt % | Maleic acid wt % | Condition |
|---|---|---|---|---|
| 1 | 19.72% | 78.90% | 1.38% | Slight crystals |
| 2 | 19.33% | 77.30% | 3.37% | clear |
| 3 | 18.69% | 74.77% | 6.54% | clear |

TABLE 13

Effect of Maleic Acid on the Solubility of Bupivacaine Dissolved in N-Methylpyrrolidone

| Vial # | % Bupivacaine | % Solvent | % Maleic acid | Condition |
|---|---|---|---|---|
| 1 | 32.68% | 65.35% | 1.97% | Clear |
| 2 | 32.89% | 65.78% | 1.32% | Clear |
| 3 | 33.11% | 66.22% | 0.67% | Crystals* |
| 4 | 37.59% | 60.14% | 2.27% | Clear |
| 5 | 37.88% | 60.60% | 1.52% | Clear |
| 6 | 38.17% | 61.06% | 0.77% | Crystals |
| 7 | 61.34% | 36.81% | 1.85% | Clear |
| 8 | 61.72% | 37.03% | 1.24% | Crystals* |
| 9 | 62.11% | 37.27% | 0.63% | Crystals |

*Crystallization occurred immediately after compounding with polyorthoester polymer.

It is claimed:

1. A method for pain management, comprising:
administering to a subject in need a composition comprising a polyorthoester, maleic acid, an aprotic solvent selected from N-methyl-2-pyrrolidone (NMP) and dimethyl sulfoxide (DMSO), and a therapeutically active agent dispersed or solubilized in the composition,
wherein the therapeutically active agent is selected from the group consisting of bupivacaine, levobupivacaine, dibucaine, mepivacaine, procaine, lidocaine, tetracaine, and ropivacaine, and
wherein the maleic acid is present in less than an equimolar amount when compared to the therapeutically active agent, such that the therapeutically active agent is present as a mixed salt-base and the composition is substantially free of crystals of the therapeutically active agent.

2. The method of claim 1, wherein the therapeutically active agent is solubilized in the composition.

3. The method of claim 1, wherein the polyorthoester is selected from polyorthoesters represented by Formulas I, II, III or IV:

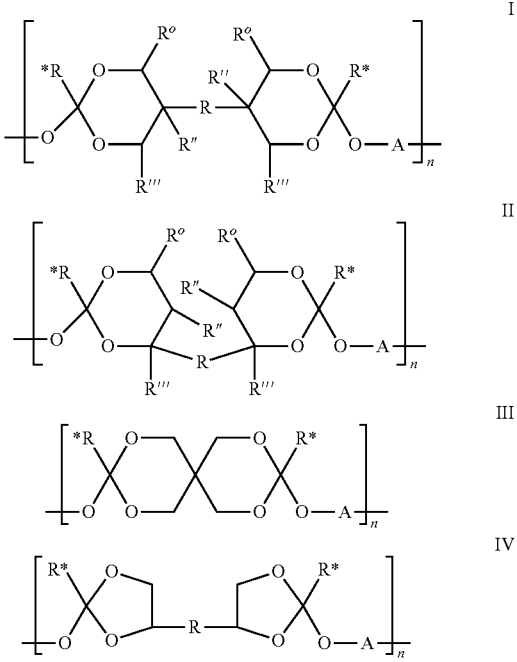

where:
R is a bond, $-(CH_2)_a-$, or $-(CH_2)_b-)-O-(CH_2)_c-$; where a is an integer of 1 to 12, and b and c are independently integers from 1 to 5;
R* is a $C_{1-4}$ alkyl;
$R^o$, R' and R''' are each independently H or $C_{1-4}$ alkyl;
n is an integer of at least 5; and
A is $R^1$, $R^2$, $R^3$, or $R^4$, where
$R^1$ is an α-hydroxy acid containing subunit

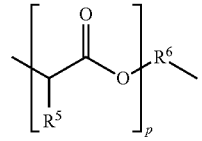

or

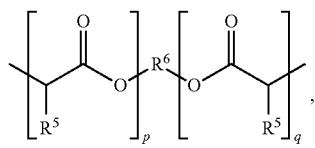

where:
p and q are integers that vary from between 1 and 20, where the average number of p or the average sum of p and q is between 1 and 7;

$R^5$ is hydrogen or $C_{1-4}$ alkyl; and
$R^6$ is selected from the group consisting of

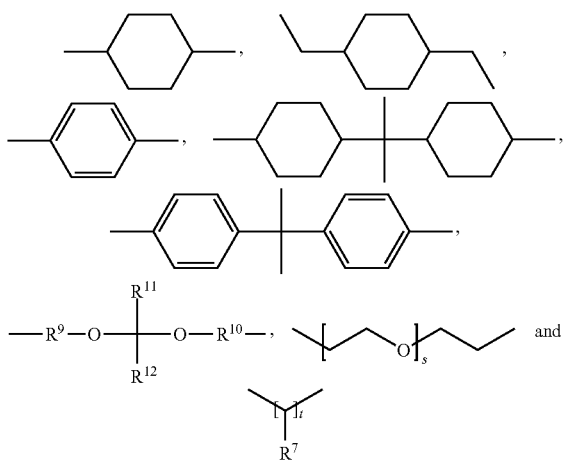

where:
s is an integer of 0 to 30;
t is an integer of 2 to 200; and
$R^7$ is hydrogen or $C_{1-4}$ alkyl;
$R^2$ is:

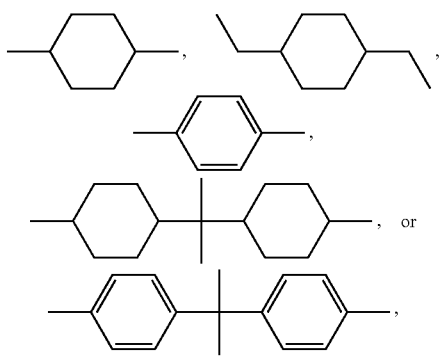

$R^3$ is:

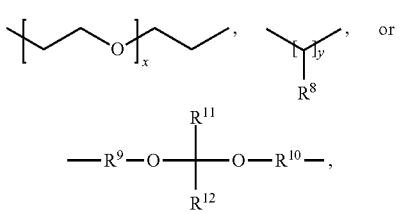

where:
x is an integer ranging from 0 to 200;
y is an integer ranging from 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl;
or $R^{11}$ and $R^{12}$ together are $C_{3-10}$ alkylene; and
$R^4$ is the residue of a diol containing at least one functional group independently selected from amide, imide, urea, and urethane groups.

4. The method of claim 1, wherein the polyorthoester is represented by Formula III:

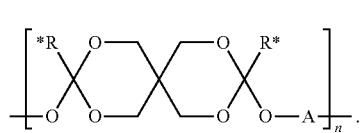

wherein:
$R^*$ is a $C_{1-4}$ alkyl, n is an integer ranging from 5 to 400, and A in each subunit is $R^1$ or $R^3$,
wherein:
$R^1$ is

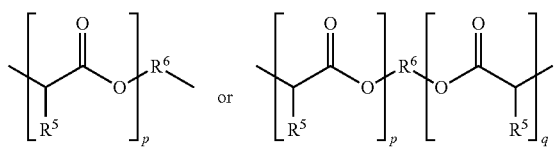

where p and q are each independently integers that range from between about 1 to 20, each $R^5$ is independently hydrogen or $C_{1-4}$ alkyl; and $R^6$ is:

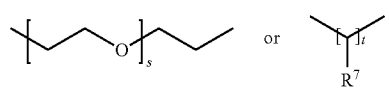

where s is an integer from 0 to 10; t is an integer from 2 to 30; and $R^7$ is hydrogen or $C_{1-4}$ alkyl,
$R^3$ is:

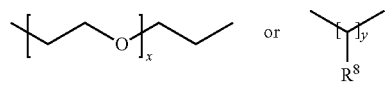

and x is an integer ranging from 1 to 100; y is an integer in a range from 2 to 30; and $R^8$ is hydrogen or $C_{1-4}$ alkyl.

5. The method of claim 1, wherein said administering comprises instilling the composition to a surgical site.

6. A method of prophylactic treatment of pain to a patient in need thereof, comprising:
locally administering to the patient in need a composition comprising a polyorthoester, maleic acid, an aprotic solvent selected from N-methyl-2-pyrrolidone (NMP) and dimethyl sulfoxide (DMSO), and an amino-amide anesthetic a therapeutically active agent dispersed or solubilized in the composition,
wherein the therapeutically active agent is selected from the group consisting of bupivacaine, levobupivacaine, dibucaine, mepivacaine, procaine, lidocaine, tetracaine, and ropivacaine, and
wherein the maleic acid is present in less than an equimolar amount when compared to the therapeutically active agent amino-amide anesthetic, such that the therapeutically active agent is present as a mixed salt-base and the composition is substantially free of crystals of the therapeutically active agent.

7. The method of claim 6, wherein said locally administering is dispensing from a needle.

8. A method for managing or treating post-operative pain, comprising:

administering to a subject in need a composition comprising a polyorthoester, maleic acid, an aprotic solvent selected from N-methyl-2-pyrrolidone (NMP) and dimethyl sulfoxide (DMSO), and an amino-amide anesthetic a therapeutically active agent dispersed or solubilized in the composition, wherein the therapeutically active agent is selected from the group consisting of bupivacaine, levobupivacaine, dibucaine, mepivacaine, procaine, lidocaine, tetracaine, and ropivacaine, and wherein the maleic acid is present in less than an equimolar amount when compared to the therapeutically active agent amino-amide anesthetic, such that the therapeutically active agent is present as a mixed salt-base and the composition is substantially free of crystals of the therapeutically active agent.

9. A method for reducing or preventing post-operative pain, comprising:

administering to a subject in need a composition comprising a polyorthoester, maleic acid, an aprotic solvent selected from N-methyl-2-pyrrolidone (NMP) and dimethyl sulfoxide (DMSO), and a therapeutically active agent dispersed or solubilized in the composition, wherein the therapeutically active agent is selected from the group consisting of bupivacaine, levobupivacaine, dibucaine, mepivacaine, procaine, lidocaine, tetracaine, and ropivacaine, and wherein the maleic acid is present in less than an equimolar amount when compared to the therapeutically active agent, such that the therapeutically active agent is present as a mixed salt-base and the composition is substantially free of crystals of the therapeutically active agent.

* * * * *